United States Patent
Lampropoulos et al.

(10) Patent No.: US 10,350,019 B2
(45) Date of Patent: Jul. 16, 2019

(54) MEDICAL INSTRUMENT RECEPTACLE AND RELATED METHODS

(71) Applicant: Merit Medical Systems, Inc., South Jordan, UT (US)

(72) Inventors: Fred Lampropoulos, Salt Lake City, UT (US); Jim Mottola, West Jordan, UT (US); Richard Jenkins, Bluffdale, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 372 days.

(21) Appl. No.: 14/994,803

(22) Filed: Jan. 13, 2016

(65) Prior Publication Data

US 2016/0206394 A1 Jul. 21, 2016

Related U.S. Application Data

(60) Provisional application No. 62/104,502, filed on Jan. 16, 2015, provisional application No. 62/209,176, filed on Aug. 24, 2015.

(51) Int. Cl.

| | |
|---|---|
| *A61B 50/00* | (2016.01) |
| *A61B 50/20* | (2016.01) |
| *A61M 25/09* | (2006.01) |
| *B65D 81/22* | (2006.01) |
| *A61M 25/00* | (2006.01) |
| *A61B 50/22* | (2016.01) |
| *A61B 50/30* | (2016.01) |
| *A61B 90/70* | (2016.01) |

(52) U.S. Cl.
CPC .............. *A61B 50/20* (2016.02); *A61B 50/22* (2016.02); *A61B 50/30* (2016.02); *A61M 25/002* (2013.01); *A61M 25/09* (2013.01); *B65D 81/22* (2013.01); *A61B 90/70* (2016.02); *A61B 2050/005* (2016.02); *A61B 2050/006* (2016.02); *A61B 2050/0051* (2016.02); *A61B 2050/3008* (2016.02); *A61B 2050/3009* (2016.02)

(58) Field of Classification Search
CPC .... B05C 3/08; B05C 3/04; B05C 3/02; B05C 3/00; A61M 25/002; A61M 25/0111; A61M 25/0113
USPC ....... 134/94.1, 95.2, 166 C, 167 C, 170, 171
See application file for complete search history.

(56) References Cited

U.S. PATENT DOCUMENTS

| | | | | |
|---|---|---|---|---|
| 2,986,918 A | * | 6/1961 | Widigen ................. | D06F 95/00 474/112 |
| 5,769,222 A | * | 6/1998 | Banerian ............. | A61M 25/002 206/210 |

(Continued)

OTHER PUBLICATIONS

Ring Master, Guide Wire Basin, Merit Medical Systems, Inc., Nov. 17, 2008.

*Primary Examiner* — Steven A. Reynolds
*Assistant Examiner* — Javier A Pagan
(74) *Attorney, Agent, or Firm* — Stoel Rives LLP

(57) ABSTRACT

A medical device, assembly, or kit may be used to hold a plurality of elongate medical instruments, such as guidewires, catheters, etc. A guidewire holder may include a reservoir for holding a liquid and one or more separators for segregating the guidewires from each other. In some instances, the guidewire holder can hold a coiled guidewire such that the guidewire is in contact with liquid held by the reservoir.

19 Claims, 21 Drawing Sheets

(56) References Cited

U.S. PATENT DOCUMENTS

| | | | |
|---|---|---|---|
| 6,547,072 B2 | 4/2003 | Whiting et al. | |
| 9,192,741 B1 * | 11/2015 | Najibi | B65D 81/22 |
| 2015/0034122 A1 | 2/2015 | Mottola et al. | |

* cited by examiner

MEDICAL INSTRUMENT RECEPTACLE AND RELATED METHODS

RELATED APPLICATIONS

This application claims priority to U.S. Provisional Application No. 62/104,502 filed on Jan. 16, 2015 and titled "Medical Instrument Receptacle and Related Methods" and U.S. Provisional Application No. 62/209,176 filed on Aug. 24, 2015 and titled "Medical Instrument Receptacle and Related Methods," both of which are hereby incorporated by reference in their entireties.

TECHNICAL FIELD

This application generally relates to medical devices and assemblies for storage or organization of elongate medical instruments, such as guidewires. Further, in some instances, such devices may be configured to hydrate or otherwise keep the elongate medical instrument in contact with (e.g., immersed within) a liquid. Some medical devices or assemblies include a reservoir for holding liquid and one or more separators for segregating guidewires from each other and maintaining the guidewires in contact with the liquid.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
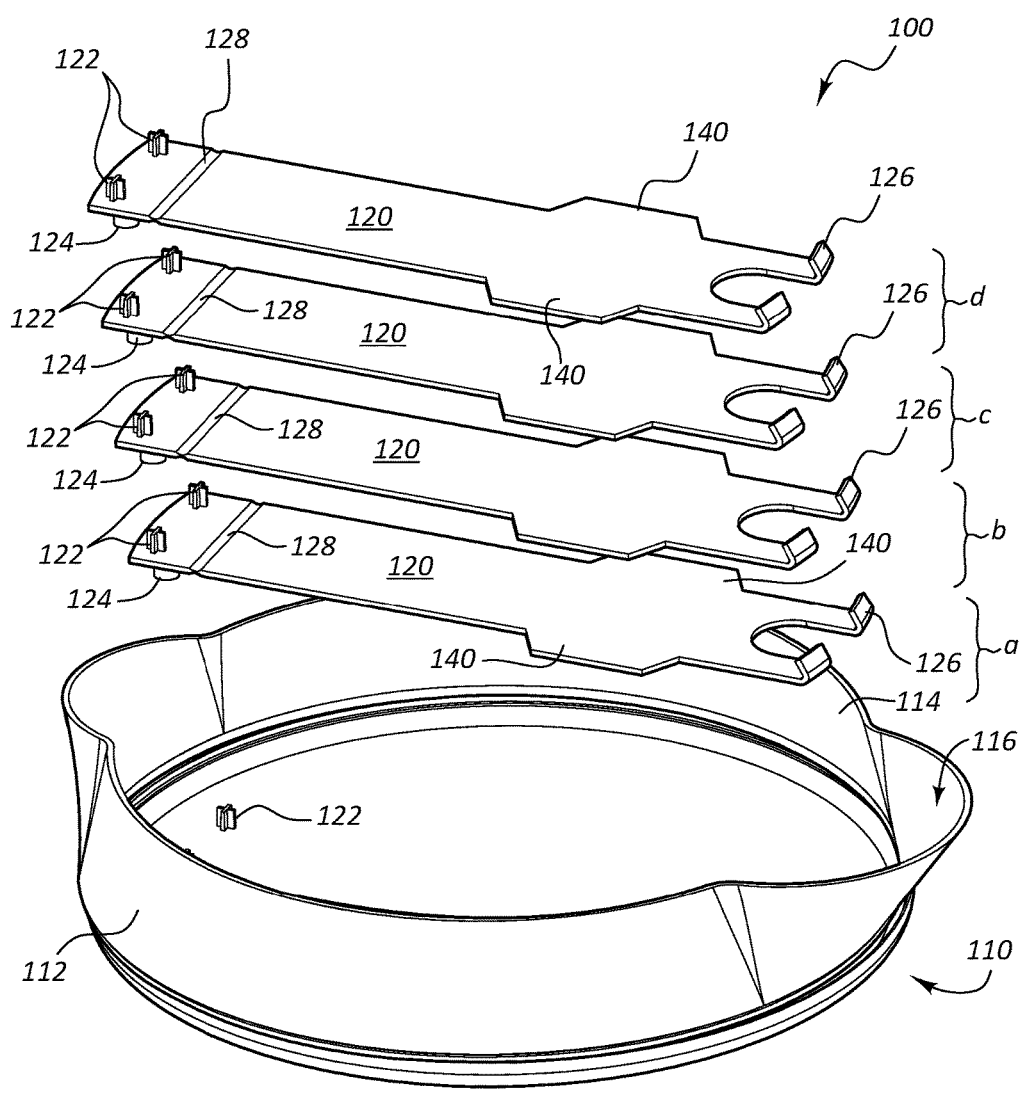
FIG. 1 is an exploded perspective view of a guidewire holder.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to" and "coupled to" are used in their ordinary sense, and are broad enough to refer to any suitable coupling or other form of interaction between two or more entities, including mechanical, fluid and thermal interaction. Two components may be coupled to each other even though they are not in direct contact with each other. The phrases "attached to" or "directly attached to" refer to interaction between two or more entities which are in direct contact with each other and/or are separated from each other only by a fastener of any suitable variety (e.g., an adhesive).

The terms proximal and distal refer to opposite ends of a device or component. For example, when used in connection with some separators disclosed herein, the term "proximal" may refer to the region of the separator adjacent to the location where the separator is configured to couple to either the reservoir or another separator. The term "distal," when used in connection with a separator, refers to the opposite end of the separator (e.g., the end furthest from the location where the separator is configured to couple to the reservoir or another separator).

Guidewires may be used to direct a catheter or other elongate instrument within the vascular system of a patient. For example, a guidewire may be placed through a blood vessel of a patient and directed by a medical practitioner to a particular region within the patient's body. A catheter may then be advanced over the guidewire so that the catheter is positioned proximate to the desired region within the patient. The catheter may then be used to carry out a desired medical procedure.

In some instances, guidewires are stored in a liquid (e.g., water, saline, antibacterial solution, and/or anticoagulant) prior to their use in a medical procedure. Hydration of the guidewire, such as by storage in a liquid, may increase the lubricity of the guidewire as it is advanced within a patient, protect the guidewire from contaminants, and/or reduce coagulation around the guidewire once it is inserted into the patient. Storage in a liquid may provide other advantages as well.

Some guidewires can present storage difficulties due to, inter alia, their substantial length and the characteristics (e.g., resiliency) of the materials from which they are made. For instance, some guidewires that are coiled to facilitate handling and storage will, due to the resiliency of the materials from which they are made, tend to uncoil, spring open, and/or expand coil size unless the guidewire is restrained in some fashion. Thus, in some instances, receptacles for receiving a guidewire should restrain the guidewire so that it remains in a coiled state.

The storage of guidewires can be particularly difficult when a practitioner attempts to store multiple coiled guidewires in a single reservoir (e.g., a basin). Although the storage of multiple guidewires in a single reservoir can be advantageous in some respects (e.g., the guidewires can be stored in a relatively small space and immersed in liquid by filling only a single reservoir), a practitioner may find it difficult to (1) identify a desired guidewire from among the multiple guidewires in a reservoir, and (2) remove that particular guidewire without disturbing the other guidewire(s) in the reservoir.

Some of the receptacles (e.g., guidewire holders) disclosed herein include separators for separating a particular coiled guidewire from one or more neighboring guidewires in a reservoir. In some embodiments, the separators also hold or otherwise maintain the coiled guidewire such that the guidewire is partially or completely submerged in a liquid.

Figure 2:
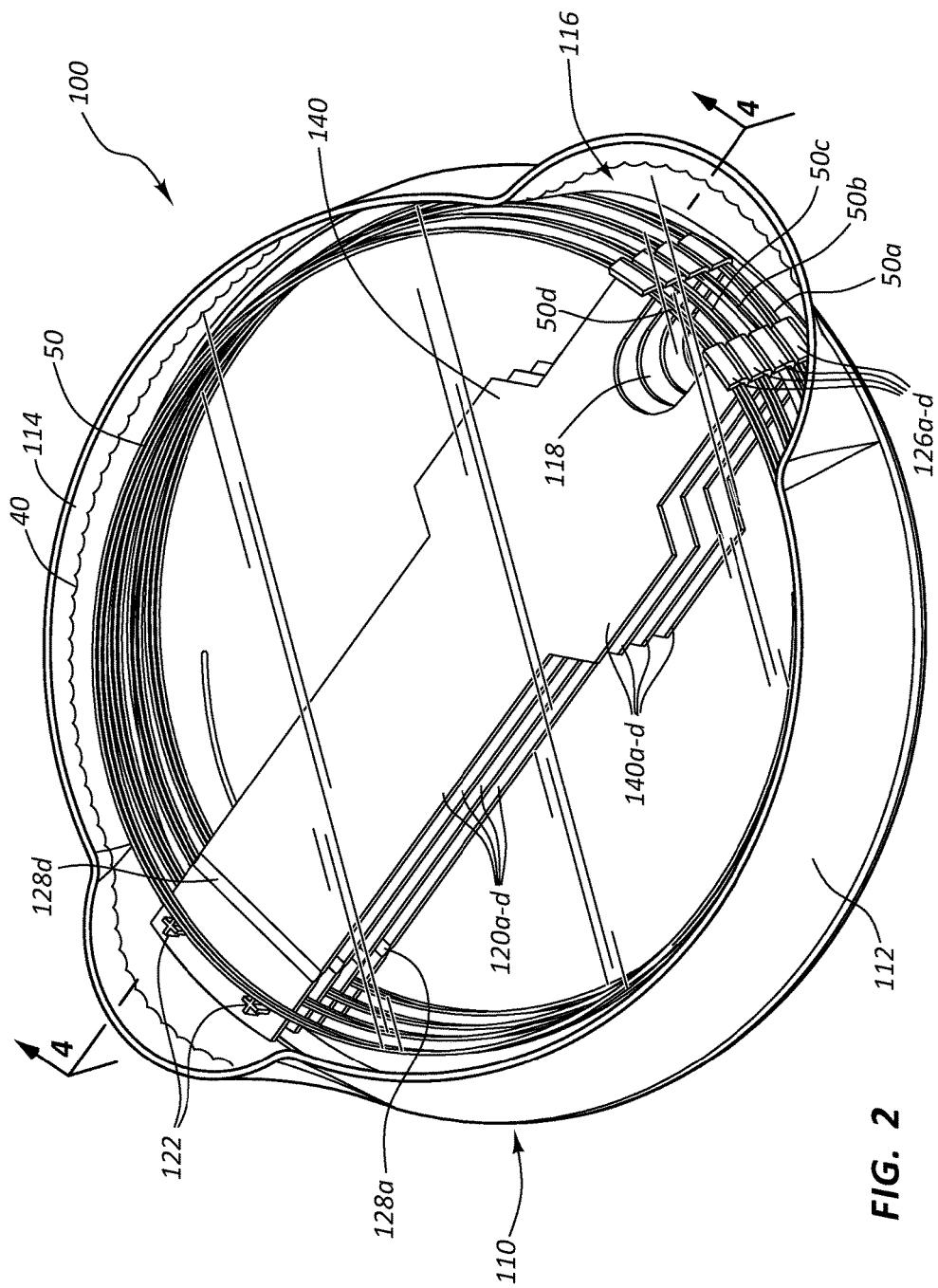
FIG. 2 is a perspective view of the guidewire holder of FIG. 1 with the separators in a lowered position.
Figure 3:
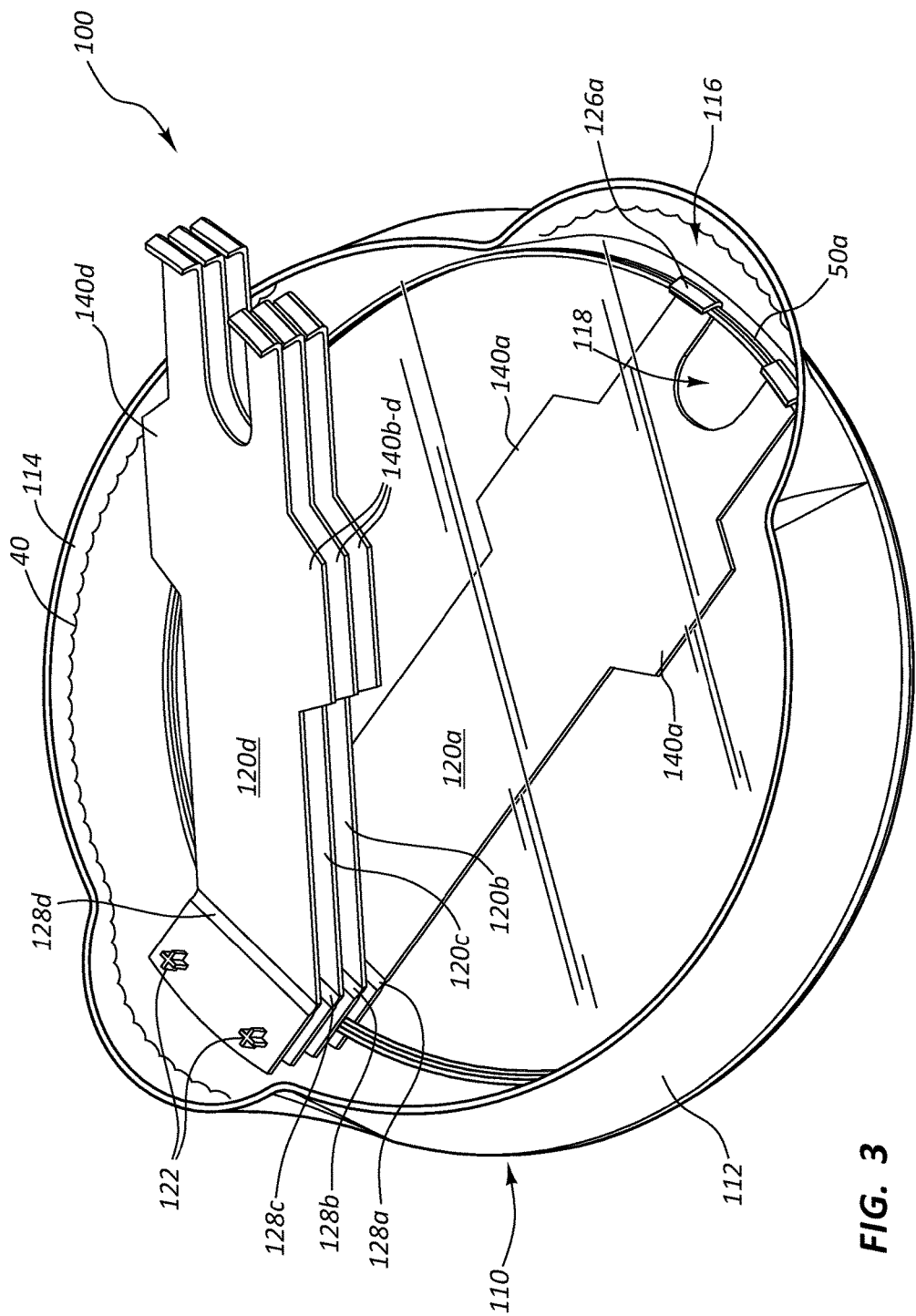
FIG. 3 is a perspective view of the guidewire holder of FIG. 1 with some of the separators in a raised position.
Figure 4:
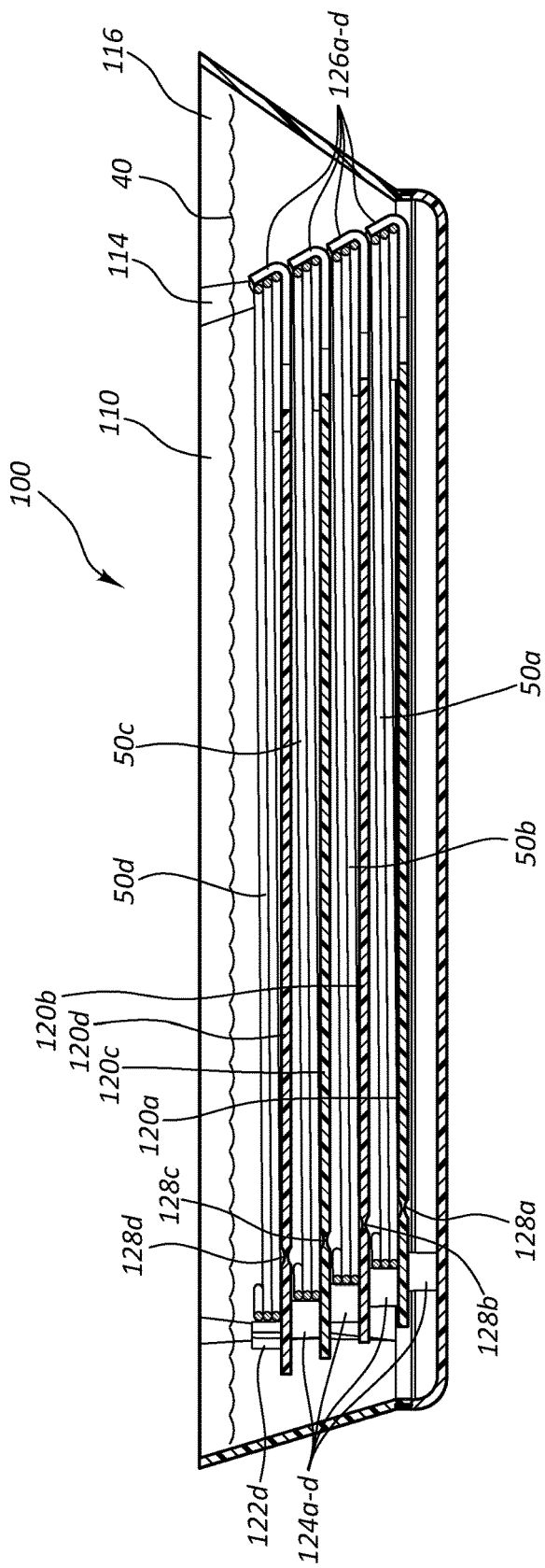
FIG. 4 is a cross-sectional side view of the guidewire holder of FIG. 1.

FIGS. 1-4 depict a guidewire holder 100. More particularly, FIG. 1 provides an exploded perspective view of the guidewire holder 100. FIG. 2 provides a perspective view of the guidewire holder 100 with separators 120 in a lowered position to maintain a plurality of guidewires 50 below the surface of a liquid 40. FIG. 3 is a perspective view of the guidewire holder 100 with three separators 120 in a raised position and a coiled guidewire held in place by the lowest separator 120. FIG. 4 is a cross-sectional side view of the guidewire holder 100 through line 4-4 of FIG. 2.

With reference to FIGS. 1-4, the guidewire holder 100 includes a reservoir 110 (e.g., a basin) and a plurality of separators 120. The reservoir 110 may be shaped in any suitable manner. For example, in the embodiment depicted in FIGS. 1-4, the reservoir 110 is a relatively shallow pan of generally circular shape. In some circumstances, the reservoir 110 is filled with liquid 40 either prior to or after placement of one or more guidewires 50 in the guidewire holder 100. In the illustrated embodiment, the reservoir 110 comprises an outer periphery 112 that is curved inward to present a concave inner surface 114 to a coiled guidewire 50 disposed within the reservoir 110. Since coiled guidewires 50 may tend to uncoil, spring open, and/or expand in size, the interaction of the concave inner surface 114 to the coiled guidewire 50 may retain the guidewire 50 within the outer periphery 112 of the reservoir 110. This interaction prevents the guidewire 50 from working out of the guidewire holder 100. The reservoir 110 of FIG. 1 also includes an outcropping to create an access area 116 that is configured to suspend a portion of the guidewire 50 away from an outer periphery 112 of the reservoir 110. In other words, the reservoir 110 comprises an outer periphery 112 that protrudes outward to form an access area 116 to facilitate grasping of a coiled guidewire 50 by a practitioner. This access area 116 facilitates insertion and/or removal of a guidewire 50 from the guidewire holder 100. The access area 116 may also be used as a spout to discard liquid in the reservoir 110 at the conclusion of a medical procedure.

In the embodiment depicted in FIGS. 1-3, a plurality of separators 120 are configured to be disposed within the reservoir 110. One or more of the plurality of separators 120 may be configured to attach or otherwise couple to the reservoir 110. More particularly, one or more separators 120 may comprise a downward protrusion 124 (e.g., a hollow cylindrical protrusion) that is configured to couple to an upward protrusion 122 (e.g., an x-shaped protrusion) on the reservoir 110. The one or more separators 120 may couple to the reservoir 110 via a snap fit-type mechanism. In other embodiments, the plurality of separators 120 may be disposed within but not coupled to the reservoir 110.

As depicted in FIGS. 1-4, each separator 120 of the plurality of separators 120 is generally elongate in shape and comprises a proximal portion and a distal portion. The proximal portions of each of the depicted separators 120 are configured to attach or otherwise couple to one or more of another separator 120 and the reservoir 110. For example, a proximal portion of a first separator 120a comprises a fastener for coupling the first separator 120a to an adjacent second separator 120b. More particularly, in the embodiment depicted in FIGS. 1-4, an x-shaped upward protrusion 122a is configured to attach to a cylindrical downward protrusion 124b via snap-fit type mechanism. The distal portion of a separator 120 (e.g., second separator 120b) is configured to be displaced relative to an adjacent separator 120 (e.g., first separator 120a) when the separators 120 are coupled to one another via interactions that occur in the proximal portions of each separator 120 (compare FIGS. 2 and 3).

The upward protrusions 122 and downward protrusions 124 on an individual separator 120 need not be vertically aligned. For example, as shown in FIG. 4, the upward protrusion 122 is disposed proximal of the downward protrusion 124. Thus, coupling of a first separator 120a to second separator 120b causes the separators 120 to be offset from one another. Stated differently, the proximal end of a second separator 120b may be disposed proximal of the proximal end of a first separator 120a due to the manner in which the separators 120 are coupled to one another.

A separator 120 may also comprise a catch 126. In the depicted embodiment, the catches 126 are disposed at or adjacent to the distal ends of the separators 120. The catch 126 comprises a concave inner surface (i.e., an inner surface that is concave with respect to a guidewire 50 that is disposed within the guidewire holder 100). The concave inner surface of the catch 126 interacts with the guidewire 50 to retain the guidewire 50 within the catch 126, resisting the tendency of the coiled guidewire 50 to expand. In other words, the concave surface of the catch 126 may prevent the guidewire 50 from working out of the guidewire holder 100.

In some embodiments, each separator 120 of the plurality of separators 120 is substantially the same size and shape. By manufacturing the separators 120 such that each separator 120 is essentially the same size and shape, similar components, materials, and processes may be used to create each individual separator 120. For example, in some embodiments, each separator 120 is formed from the same mold. In other embodiments, the separators are uniquely shaped.

A separator 120 may comprise one or more wings or tabs 140 that extend from the main portion of the separator 120. For example, as depicted in FIGS. 1-4, tabs 140 extend laterally from the main portion of separator 120. The tabs 140 are used to facilitate displacement of one separator 120 relative to another separator 120. For instance, a practitioner may grasp or otherwise use a tab 140 to lift up a distal portion of a second separator 120b to separate the second separator 120b from a first separator 120a (compare FIGS. 2 and 3). Upward displacement of the tab 140 causes the distal portion of the separator 120 to pivot about a hinge 128, causing the distal portion of the separator 120 to be disposed upward relative to the proximal portion of the separator 120.

In the embodiment depicted in FIG. 4, the hinge 128 is formed from a region of the separator 120 that is of reduced thickness relative to other regions of the separator 120. One of ordinary skill in the art, with the benefit of this disclosure, will recognize that many other mechanisms may be used to allow a distal portion of a separator 120 to move (e.g., swing) upward relative to a proximal portion of the separator 120. For example, in some embodiments, each separator is formed from a compliant or flexible material, allowing the distal end of each separator to bend upward relative to the proximal portion of the separator although the separator lacks an identifiable hinge. By displacing a distal end of a separator in a manner described above, a practitioner may access each separator individually to insert or remove a coiled guidewire 50.

In some embodiments, the tabs 140 include a label or other indicia to indicate to the practitioner which guidewire 50 is supported by the particular separator 120. In some embodiments, a label or other indicia is placed at one or more other locations on a separator 120. Indicia used in connection with the medical devices disclosed herein may include numbers, letters, symbols, shapes, or other features. In some instances, the tabs 140 (or one or more other portions of the separator 120) are configured such that a practitioner can mark the separator 120 with indicia of the practitioner's choice. For example, a practitioner may use a marker to place a label on individual tabs 140, thereby customizing the separators for a particular use. Further, in some embodiments, the separators 120 are color-coded such that each separator 120 is a different color.

In the embodiment depicted in FIGS. 1-4, the plurality of separators 120 are configured to keep a plurality of coiled guidewires 50 in contact with (e.g., submerged within) liquid held by a reservoir 110. Each separator 120 of the plurality of separators 120 receives and retains a coiled guidewire 50 and separates the coiled guidewire 50 from an adjacent coiled guidewire 50 that is received and retained by an adjacent separator 120 of the plurality of separators 120.

An exemplary process for preparing a plurality of guidewires 50 for use in a medical procedure is outlined below. First, a practitioner removes a first guidewire 50a (e.g., the last guidewire to be used in a medical procedure) from its packaging, coils the first guidewire 50a to an appropriate size (if necessary), lifts up the distal ends of the top separators 120d, 120c, and 120b, and inserts the first guidewire 50a into the guidewire holder 100. A guidewire 50a inserted into the guidewire holder 100 in such a manner is held in place due, at least in part, to interaction with the lowest separator 120a. For example, the catch 126a of the separator 120a tends to cause the guidewire 50 to remain in a coiled state within the guidewire holder 100.

A second guidewire 50b is then inserted into the guidewire holder 100 in a similar manner. For instance, with the distal ends of the top separators 120d, 120c disposed in a relatively upright orientation and the remaining separators 120b, 120a in a relatively lowered orientation, the second guidewire 50b (e.g., the second-to-last guidewire to be used during the medical procedure) is inserted into the guidewire holder 100 such that the second guidewire 50b is held in place by the second separator 120b. The second separator 120b separates the first guidewire 50a (which is held by separator 120a) from the second guidewire 50b (held by separator 120b). The process may be repeated until the guidewire 50d to be used first in the medical procedure is held in place by the top separator 120d of the guidewire holder 100. With liquid in the reservoir 110, the guidewires 50 may thus remain in contact with a desired liquid 40 prior to use during a medical procedure. Different orders of placement, such as by size or user preference, are also within the scope of this disclosure.

The guidewires 50 may then be removed in substantially the reverse manner. For example, the guidewire 50d to be used first in a medical procedure is removed from the top separator 120d. Removal of a guidewire 50 from the guidewire holder 100 is facilitated by the access area 116 of the reservoir 110 and a recess 118 of the separator 120. The access area 116 and recess 118 suspend a portion of the guidewire away from both the reservoir 110 and the separator 120, thereby allowing a practitioner to more easily grasp the coiled guidewire 50 to remove it from the guidewire holder 100.

Relatedly, in some instances, a practitioner may place a plurality of elongate medical instruments, such as guidewires 50, in contact with liquid 40 in a reservoir 110. For example, a practitioner may initially place a first separator 120a in the reservoir 110 (e.g., by coupling the first separator 120a to the reservoir 110 via interaction between downward protrusions 124a of the first separator 120a and upward protrusions 122 of the reservoir 110). The practitioner then inserts a first guidewire 50a into the reservoir 110 such that first guidewire 50a is retained within the reservoir 110. The practitioner then places the second separator 120b in the reservoir 110 (e.g., by coupling the second separator 120b to the reservoir 100 via interaction between downward protrusions 124b of the second separator 120b and upward protrusions 122a of the first separator 120a). After the second separator 120b has been placed in the reservoir, a second guidewire 50b is then placed in the reservoir 110 such that the second guidewire 50b is retained within the reservoir 110. With the separators 120a, 120b and guidewires 50a, 50b disposed in this manner, the first guidewire 50a is separated from the second guidewire 50b by the second separator 120b. A practitioner may then place a third separator 120c and a third guidewire 50c into the reservoir 110 in a manner analogous to that used to place the second separator 120b and the second guidewire 50b into the reservoir 110. Additional separators 120 and guidewires 50 may be placed in the reservoir 110 in like manner.

The practitioner may place the guidewires 50 and/or separators 120 in the reservoir 110 such that the guidewires 50 are spatially arranged based on parameters of a therapeutic procedure. For example, in some embodiments, the practitioner assembles a plurality of separators 120 in the reservoir 100 according to some type of indicia that is associated with the separators 120. Such indicia may indicate, among other things, (1) a particular arrangement for placing the separators 120 in the reservoir 110 and/or (2) a particular guidewire 50 that is to be associated with the particular separator 120. In some circumstances, the indicia is provided by a practitioner who marks one or more separators 120 based on the parameters of a therapeutic procedure. Thus, if the indicia correspond with the requirements of a particular therapeutic procedure, arrangement of the separators 120 according to the indicia may facilitate placement of guidewires 50 in the reservoir such that the guidewires 50 are in a spatial arrangement that it suited for the procedure to be carried out by the practitioner.

Figure 5:
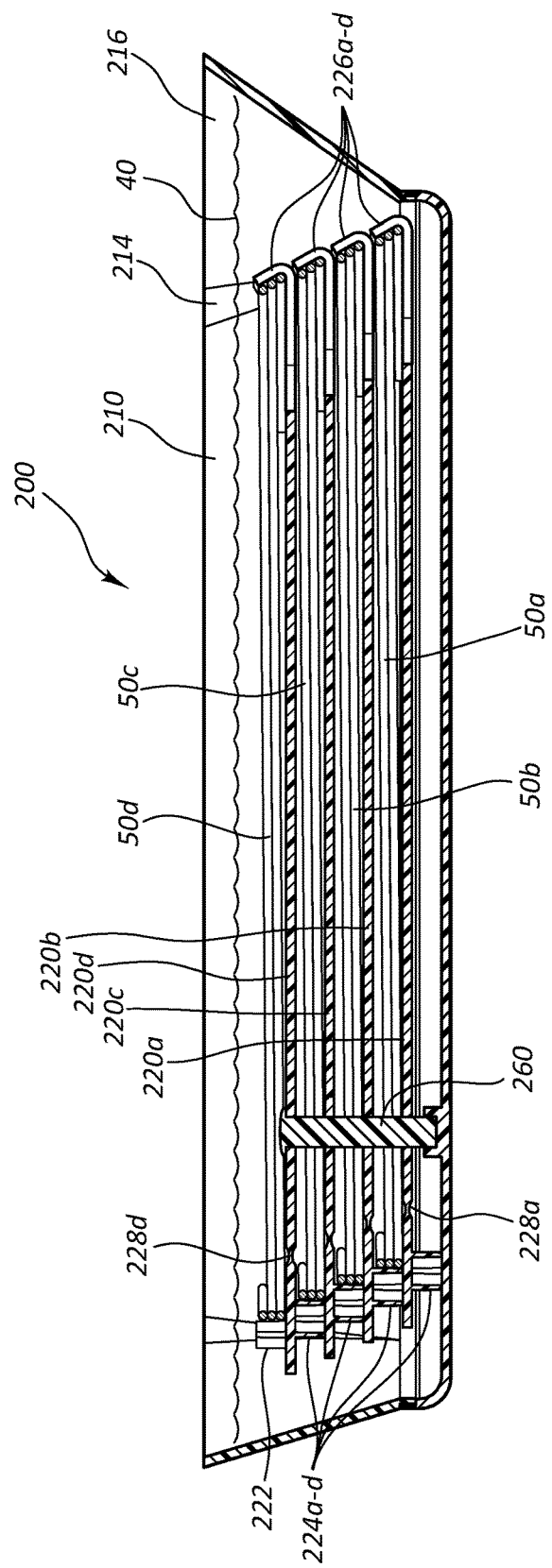
FIG. 5 is a cross-sectional side view of a guidewire holder, according to another embodiment.

FIG. 5 is a cross-sectional schematic view of a guidewire holder 200. The guidewire holder 200 resembles the guidewire holder 100 described above in certain respects. Accordingly, like features are designated with like reference numerals, with the leading digits incremented to "2." For example, the embodiment depicted in FIG. 5 includes a reservoir 210 that may, in some respects, resemble the reservoir 110 of FIGS. 1-4. Relevant disclosure set forth above regarding similarly identified features thus may not be repeated hereafter. Moreover, specific features of guidewire holders and related components shown in FIGS. 1-4 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the guidewire holder 200 and related components depicted in FIG. 5. Any suitable combination of the features, and variations of the same, described with respect to the guidewire holder 100 and related components illustrated in FIGS. 1-4 can be employed with the guidewire holder 200 and related components of FIG. 5, and vice versa. This pattern of disclosure applies equally to further embodiments depicted in subsequent figures and described hereafter, wherein the leading digits may be further incremented.

As depicted in the cross-sectional schematic view provided in FIG. 5, the illustrated guidewire holder 200 comprises a reservoir 210, a plurality of separators 220, and an indexer 260. The indexer 260 is configured to allow a practitioner to control the number of separators 120 that may be lifted to access an underlying guidewire 50. For example, a first setting of the indexer 260 may fix each of the separators 120 in a lowered configuration. A second setting of the indexer 260 may allow one separator 220*d* (but not other separators 220*c*, 220*b*, 220*a*) to be raised. A second setting may allow the top two separators 220*d*, 220*c* to be raised, but not the lowest two separators 220*b*, 220*a*. The indexer 260 may have other settings as well, such as settings that allow for the raising of separators 220*b* and/or 220*a*.

To selectively control whether a particular separator 220 can be displaced relative to another separator 220, the indexer 260 may comprise one or more cams, dogs, catches, grooves, protrusions, etc. that are configured to interact with one or more separators 220. For example, the indexer 260 may comprise a variety of mechanisms for engaging with separators 220, with each mechanism disposed at a different location along the length of the indexer 260. Stated differently, the indexer 260 may include a first mechanism for interacting with a particular separator (e.g., separator 220*d*) and a second mechanism (disposed below the first mechanism) for interaction with a different separator (e.g., separator 220*c*).

Figure 6:
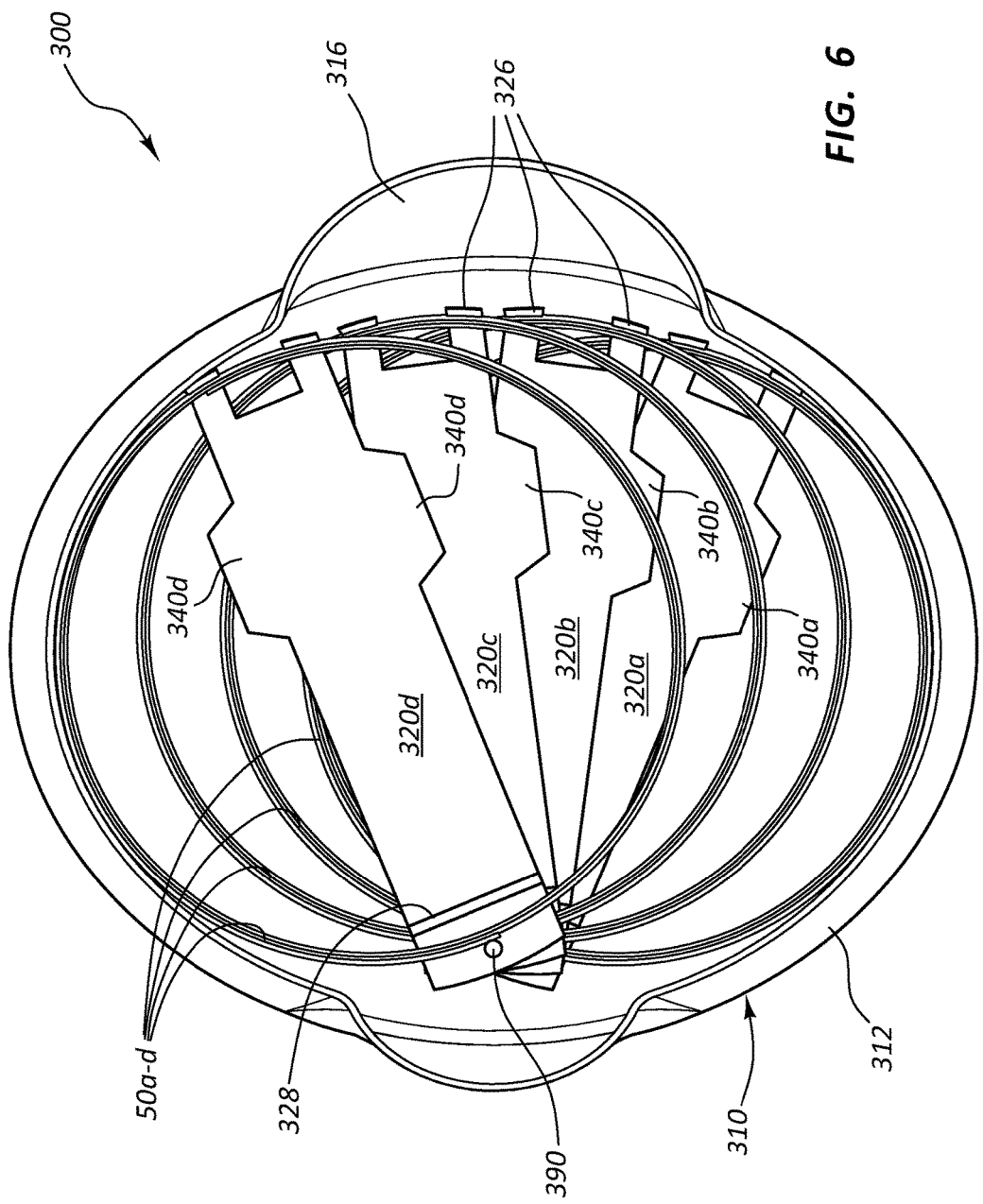
FIG. 6 is a perspective view of a guidewire holder, according to another embodiment.

FIG. 6 provides a perspective view of a guidewire holder 300 with the separators 320 in a fanned-out configuration. The guidewire holder 300 comprises a reservoir 310, a plurality of separators 320, and a pin 390 that is coupled to the proximal portions of the separators 320. In the depicted embodiment, each separator 320 of the plurality of separators 320 is configured to extend in a different direction from the pin 390 such that the plurality of separators 320 is disposed in a fanned-out configuration. In some embodiments, the separators 320 may be rotated about the pin 390. In other embodiments, the proximal portions of the separators 320 are fixed such that the plurality of separators 320 remain in a permanently fanned-out configuration. Because the fanned-out configuration prevents the distal ends of separators 320 from being disposed directly above one another, a practitioner may, in some circumstances, find it easier to raise the distal ends of the separators 320 when the 320 separators are in a fanned-out configuration.

Figure 7:
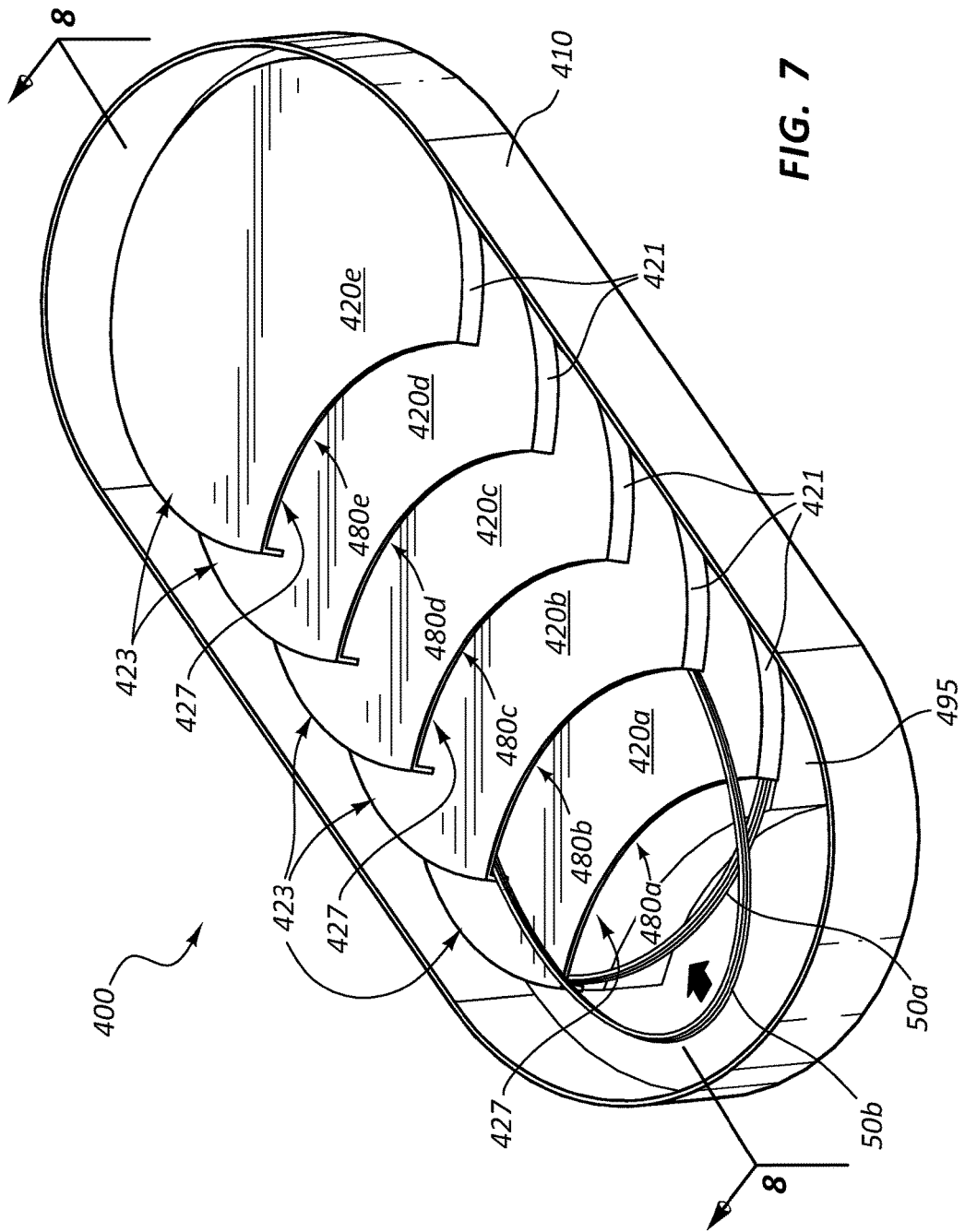
FIG. 7 is a perspective view of a guidewire holder, according to another embodiment.
Figure 8:
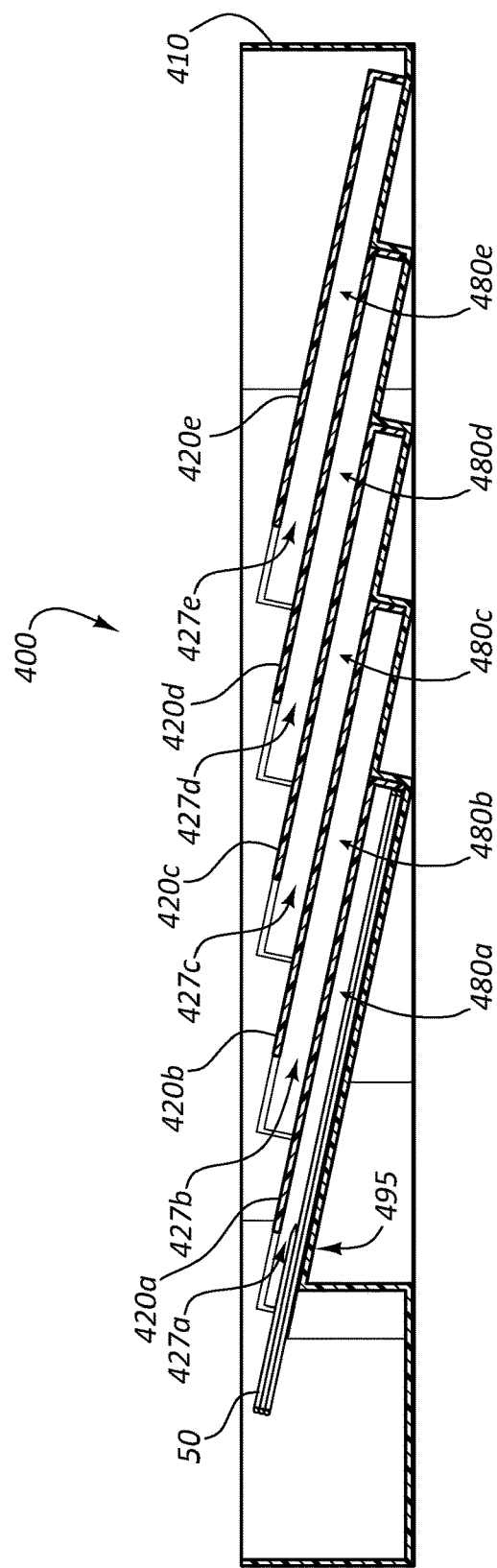
FIG. 8 is a cross-sectional side view of the guidewire holder of FIG. 7.

FIGS. 7 and 8 depict another embodiment of a guidewire holder 400. FIG. 7 provides a perspective view of a guidewire holder 400, while FIG. 8 provides a cross-sectional view through line 8-8 of FIG. 7.

With reference to FIGS. 7 and 8, the guidewire holder 400 comprises a reservoir 410, a plurality of separators 420, and a plurality of cavities 480 for receiving a guidewire 50. The separators 420 of FIG. 7 differ in some respects from those depicted in FIGS. 1-6. For example, the separators 420 are generally circular in shape with an opening for insertion of a guidewire 50. In some embodiments, one or more separators may be generally crescent-moon shaped. The separators 420 of FIGS. 7-8 form a cavity 480 that is shaped for receiving and retaining a coiled guidewire 50. Each cavity 480 is defined (in whole or in part) by an upper surface, a lower surface, a first lateral edge 421, and a second lateral edge 423. In the depicted embodiment, the first lateral edge 421 includes a first bend that is concave with respect to the second lateral edge 423. Similarly, the second lateral edge 423 includes a second bend that is concave with respect to the first lateral edge 421. The concave lateral edges 421, 423 are configured to interact with a coiled guidewire 50 to retain the guidewire 50 in the guidewire holder 400. In other words, a generally circular coiled guidewire 50 may engage with the concave lateral edges 21, 423 to secure the guidewire 50 relative to the guidewire holder 400.

A coiled guidewire 50 may be placed within a cavity 480 by inserting the guidewire 50 through an opening 427. The opening 427 may be shaped to allow insertion of a coiled guidewire 50 when the coiled guidewire 50 is compressed. Stated differently, a practitioner may need to compress a coiled guidewire 50 such that the coiled guidewire 50 adopts a non-circular (e.g., oval) configuration to fit through the opening 427 of the guidewire holder 400. Once the guidewire 50 is fully inserted into the cavity 480, the compressed coiled guidewire 50 may expand to adopt the general shape of the cavity 480. Such expansion may prevent the guidewire 50 from being inadvertently withdrawn.

Stated differently, in some embodiments, the separators 420 are generally circular in shape with openings 427 for insertion of a coiled guidewire 50. Each opening 427 is shaped and sized such that a coiled guidewire 50 must be deformed or compressed from its generally circular shape to pass through the opening 427 and into the cavity 480. Once the guidewire 50 is disposed within the cavity 480, the guidewire 50 will tend to maintain a generally circular configuration which secures the guidewire 50 within the cavity 480.

In some embodiments, separators 420 can be removed from the reservoir 410, while in other embodiments, the separators 420 are fixedly coupled (e.g., attached) to the reservoir 410. In some embodiments, the separators each comprise a top surface, a lower surface, and two lateral edges. In some embodiments, each separator 420 lacks a lower surface. For example, a separator (e.g., 420*e*) that lacks a lower surface may form a cavity 480 when stacked upon another separator (e.g., 420*d*). In some circumstances, a cavity 480 is formed by stacking a separator 420*a* on a portion of the reservoir 410 (e.g., incline 495). The stacking of separators 420 in this manner forms cavities 480 defined by the upper surface and lateral edges of an upper separator 420 and the upper surface of a lower separator 420 or the reservoir 410.

A separator 420 may be oriented such that an opening 427 formed by the separator 420 to receive a guidewire 50 is disposed higher than an oppositely positioned portion of the separator 420. For example, as depicted in FIGS. 7 and 8, the reservoir 410 comprises an incline 495 that forms a slope on which a separator 420*a* rests. The incline 495 orients the separator 420a to present the opening 427 at a higher level than other portions of the separator 420a. This incline may facilitate insertion and/or removal of a guidewire 50 into and from a cavity 480.

The separators 420 may each receive and retain a coiled guidewire 50 and separate that guidewire 50 from an adjacent guidewire 50 that is received and retained by an adjacent separator 420 of the plurality of separators 420. For instance, as depicted in FIGS. 7 and 8, a separator 420a segregates a guidewire 50a that is disposed within a first cavity 480a from an adjacent guidewire 50b that is disposed within an adjacent second cavity 480b.

Figure 9:
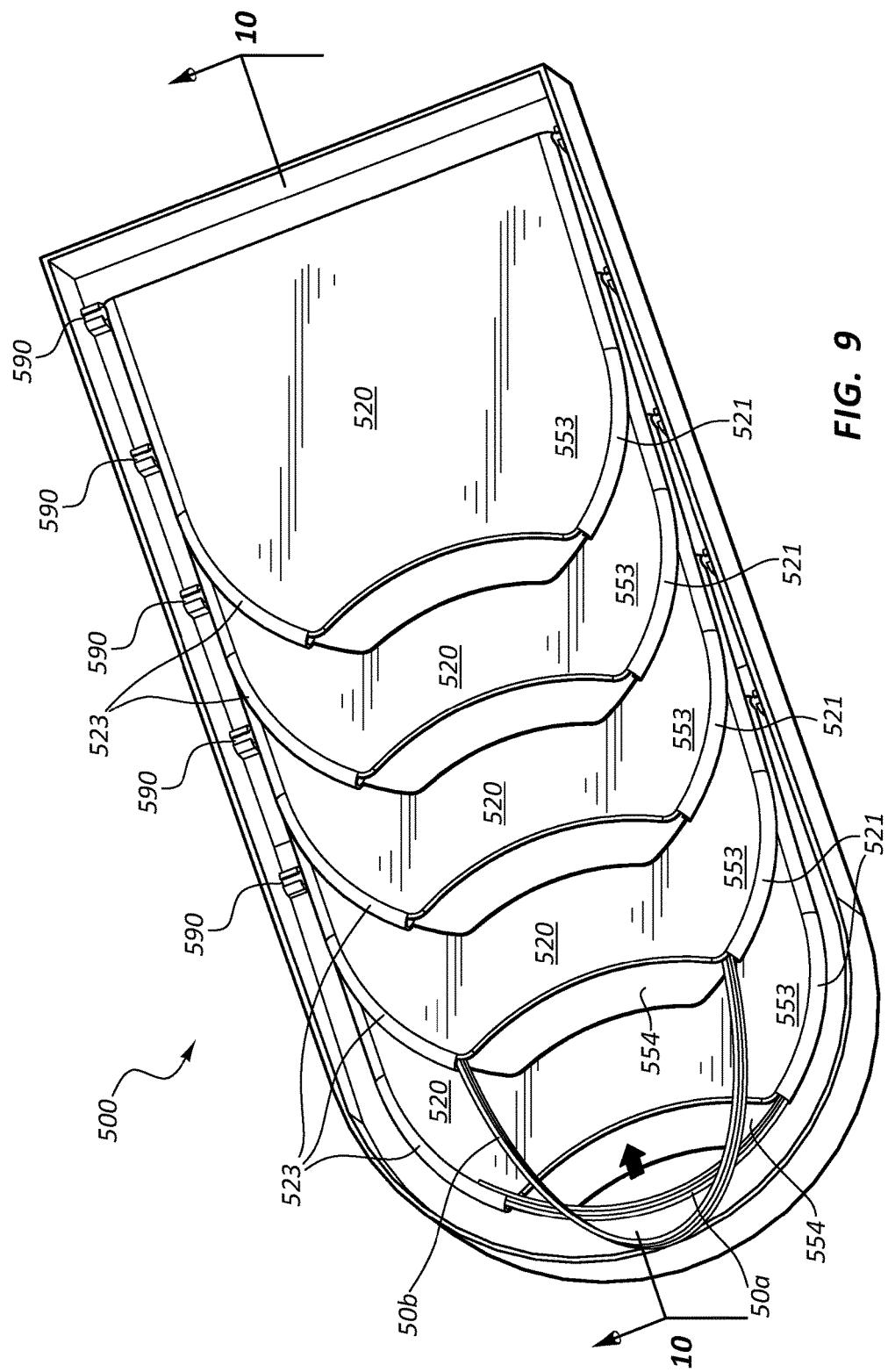
FIG. 9 is a perspective view of a guidewire holder, according to another embodiment.
Figure 10:
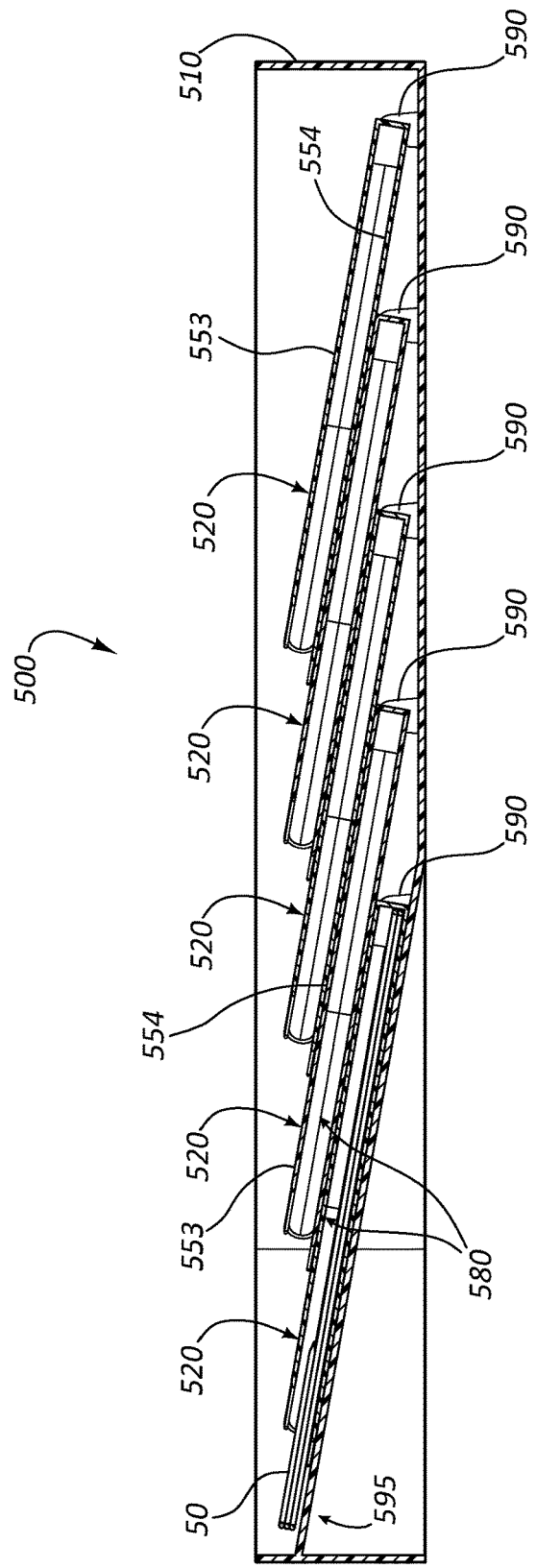
FIG. 10 is a cross-sectional side view of the guidewire holder of FIG. 9.

FIGS. 9 and 10 depict a guidewire holder 500 that resembles the guidewire holder 400 of FIGS. 7 and 8 in some respects. FIG. 9 provides a perspective view of the guidewire holder 500, while FIG. 10 provides a cross-sectional view of the guidewire holder 500 through line 10-10 of FIG. 9. The guidewire holder 500 comprises a reservoir 510 and a plurality of separators 520. The separators 520, as depicted in FIG. 9, comprise an upper surface 553, a lower surface 554, a first lateral edge 521, and a second lateral edge 523.

The separators 520 may be shaped in any suitable manner to accommodate and retain a guidewire 50. In the depicted embodiment, the upper surface 553 and lower surface 554 are generally of similar shape, with the lower surface 554 extending outward further from the opening to the cavity 580. This extended region may facilitate insertion of a guidewire 50 into the cavity 580 of each separator 520.

The separators 520 may be hingedly coupled to the reservoir 510. For example, in the embodiment depicted in FIG. 9, the hinges 590 couple separators 520 to the reservoir 510. With the separators 520 hingedly coupled to the reservoir 510, the separators 520 can be rotated from a lowered storage configuration to a more vertical orientation to facilitate removal from a guidewire 50 from the guidewire holder 500.

Figure 11A:
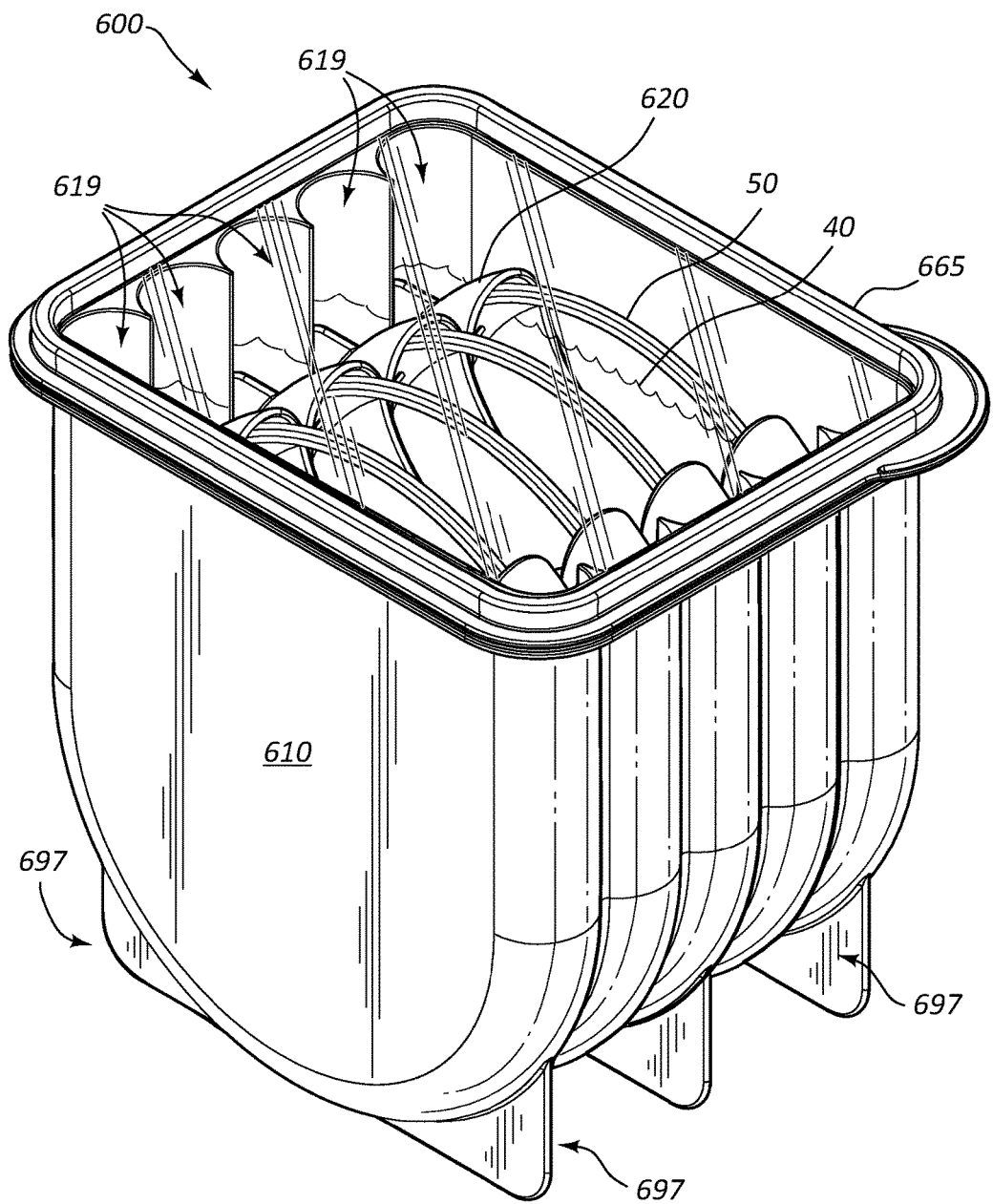
FIG. 11A is a perspective view of a guidewire holder according to another embodiment.
Figure 11B:
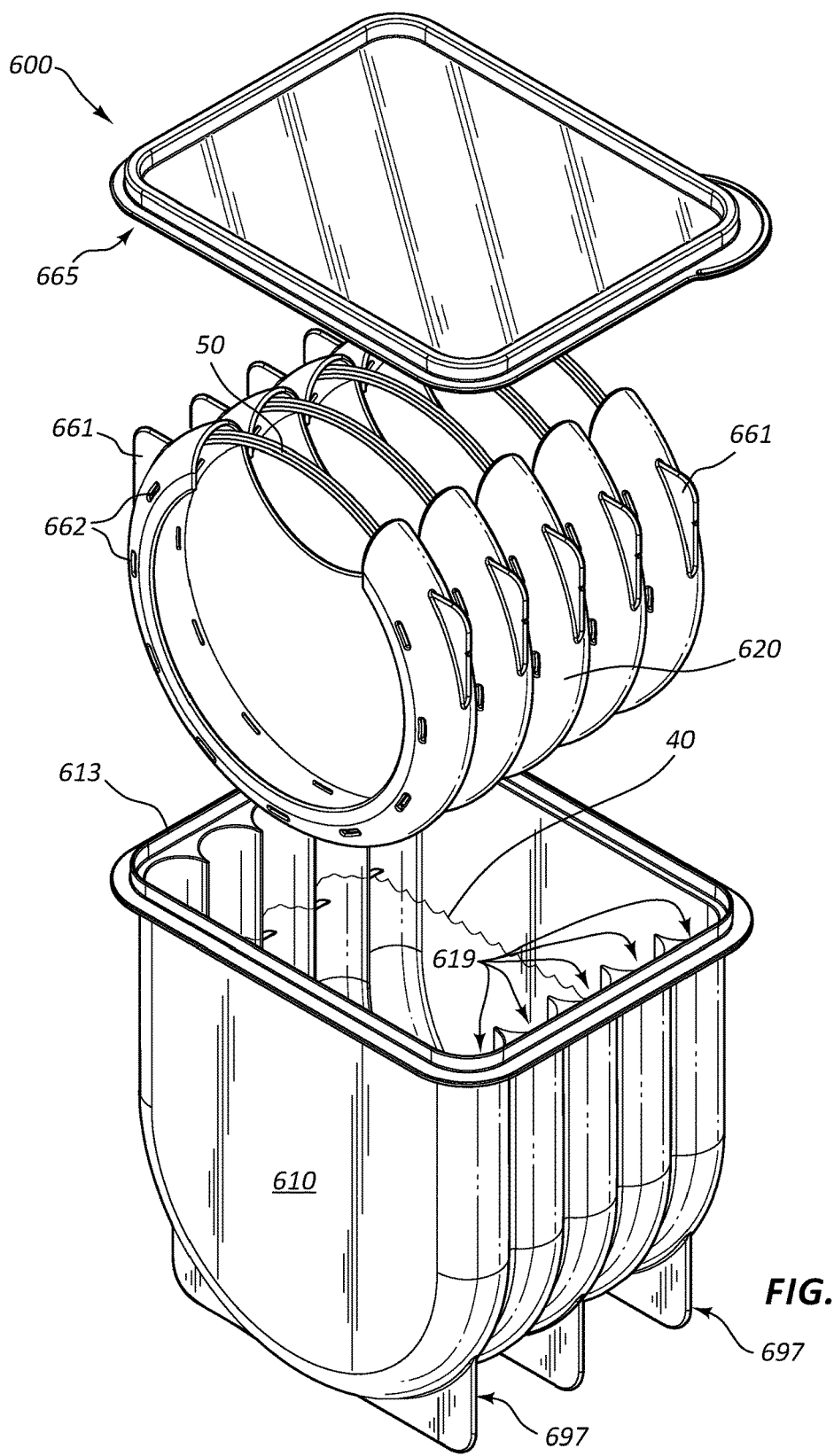
FIG. 11B is an exploded perspective view of the guidewire holder of FIG. 11A.
Figure 11D:
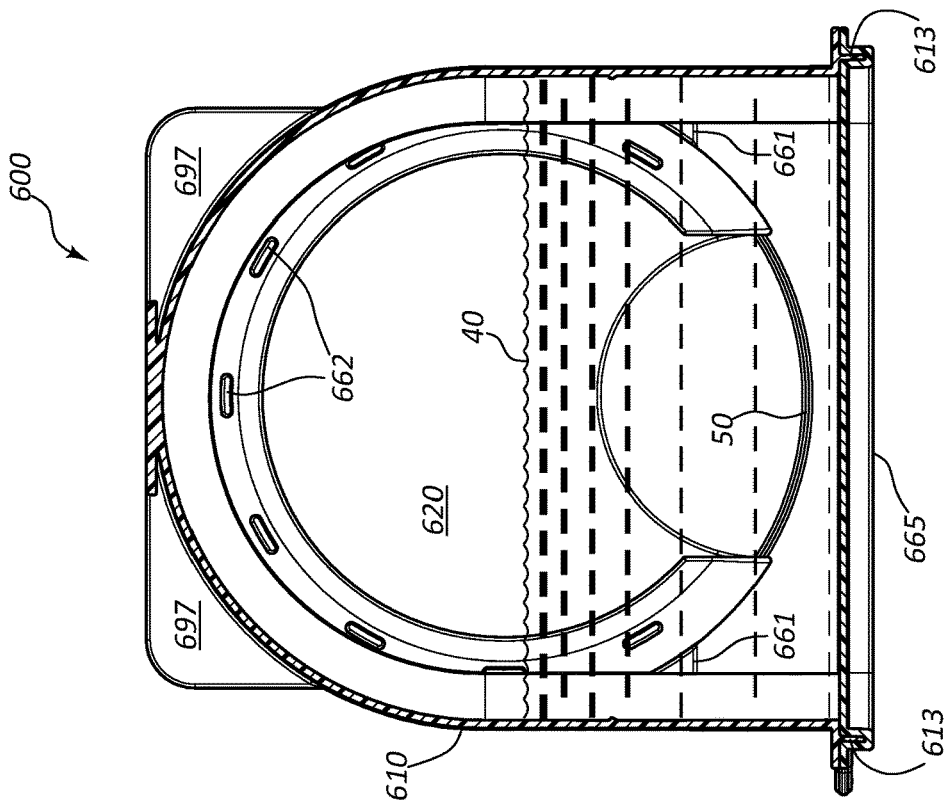
FIG. 11D is a cross-sectional front view of the guidewire holder of FIG. 11A in an upside-down configuration.
Figure 11C:
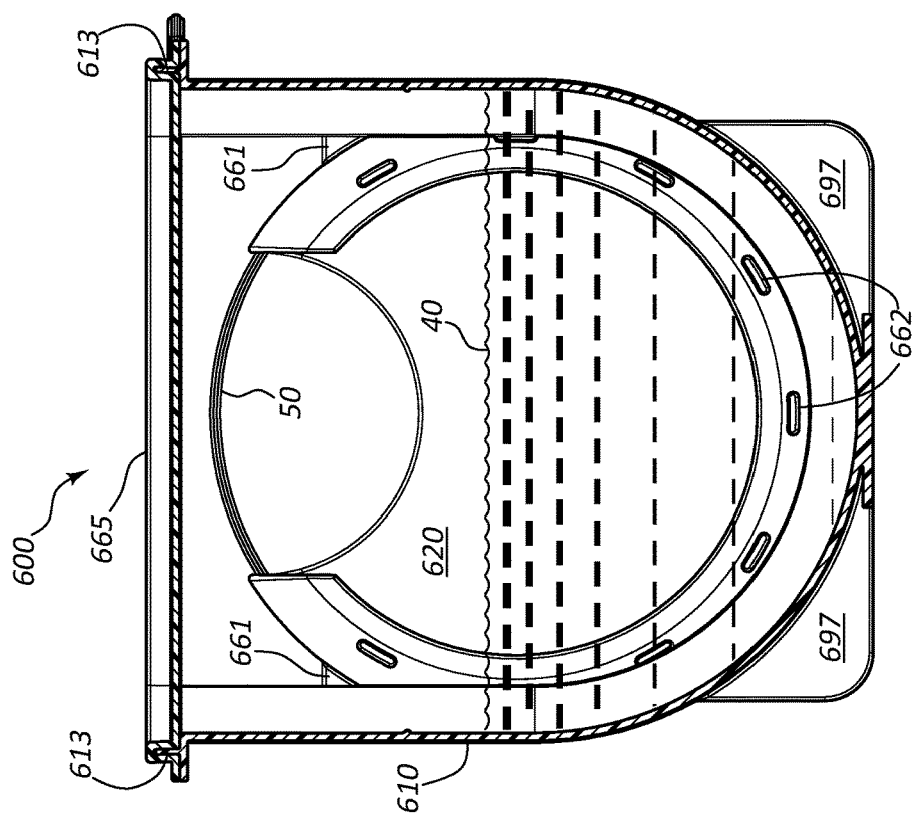
FIG. 11C is a cross-sectional front view of the guidewire holder of FIG. 11A in a right-side up configuration.

FIGS. 11A-11D depict a guidewire holder 600 according to another embodiment. More particularly, FIG. 11A provides a perspective view of a guidewire holder 600. FIG. 11B provides an exploded perspective view of the guidewire holder 600. FIG. 11C provides a cross-sectional front view of the guidewire holder 600 in right-side up configuration, while FIG. 11D depicts a cross-sectional front view of the guidewire holder 600 in an upside-down configuration.

With reference to FIGS. 11A-11D, the guidewire holder 600 includes a reservoir 610, a plurality of separators 620, and a lid 665. In the depicted embodiment, the reservoir 610, when viewed from the front, is generally U-shaped, with a plurality of legs 697 extending therefrom to stabilize the reservoir 610 in an upright configuration. The reservoir 610 includes a plurality of sections 619 that are each configured to receive a separator 620. For example, in the depicted embodiment, the reservoir 610 includes five sections 619 that are each shaped and oriented to receive a separator 620 in an upright configuration. Stated differently, in the depicted embodiment, the separators 620 may be inserted into sections 619 of the reservoir 610 such that the separators 620 are vertically oriented.

The separators 620 may be shaped in any suitable configuration for retaining a guidewire 50. For example, the separator 620 may comprise a generally horseshoe-shaped region. The horseshoe-shaped region may provide a concave inner surface that interacts with a guidewire 50 disposed therein to retain the guidewire 50 in a coiled configuration. In some embodiments, one or more of the front and back of the separator 620 may be open or closed. For example, in the depicted embodiment, a back plate extends between the arms of the horseshoe-shaped region to provide a closed back surface. In contrast, the opposite side of the horseshoe-shaped region includes an opening that allows fluid to flow freely through a front face of the separator 620. The separator 620 may also include one or more holes 662 around the horseshoe-shaped region. Such holes 662 may facilitate drainage of fluid 40 from the separator 620 when the separator 620 is lifted out of the reservoir 610. The separator 620 may have a generally circular shape, with (1) an opening at the top of the separator 620 to facilitate removal of a guidewire and/or (2) one or more protrusions 661 to limit rotation of the separator 620 within the reservoir 610.

The reservoir 610 may comprise a lip 613 disposed adjacent an upper surface of the reservoir 610. The lip 613 may be configured to interact with a lid 665 to provide a liquid-tight seal. In some embodiments, the lid 665 comprises a transparent surface that allows the practitioner to view the contents disposed within the receptacle 600 without removing the lid 665.

With reference to FIGS. 11C and 11D, when only partially filled with liquid 40, the guidewire holder 600 may be manipulated to cause the liquid 40 to hydrate or otherwise contact all portions of a guidewire 50 disposed therein. For instance, when the guidewire holder 600 is (1) just over halfway filled with liquid and (2) in an upright configuration, the fluid 40 contacts a lower portion (but not an upper portion) of the guidewire 50. The guidewire holder 600 may then be rotated from an upright configuration (see FIG. 11C) in which the lid 665 is disposed above the reservoir 610 to an upside-down configuration (see FIG. 11D) in which the lid 665 is disposed below the reservoir 610. The sealed lid 665 prevents liquid 40 from flowing out of the reservoir 610 as the guidewire holder 600 is rotated in this manner. When in the upside-down configuration, the liquid 40 contacts the portion of the guidewire 50 that was not in contact with the liquid 40 when the guidewire holder 600 was in an upright configuration. In this manner, the entire guidewire 50 may come in contact with the liquid.

Figure 12A:
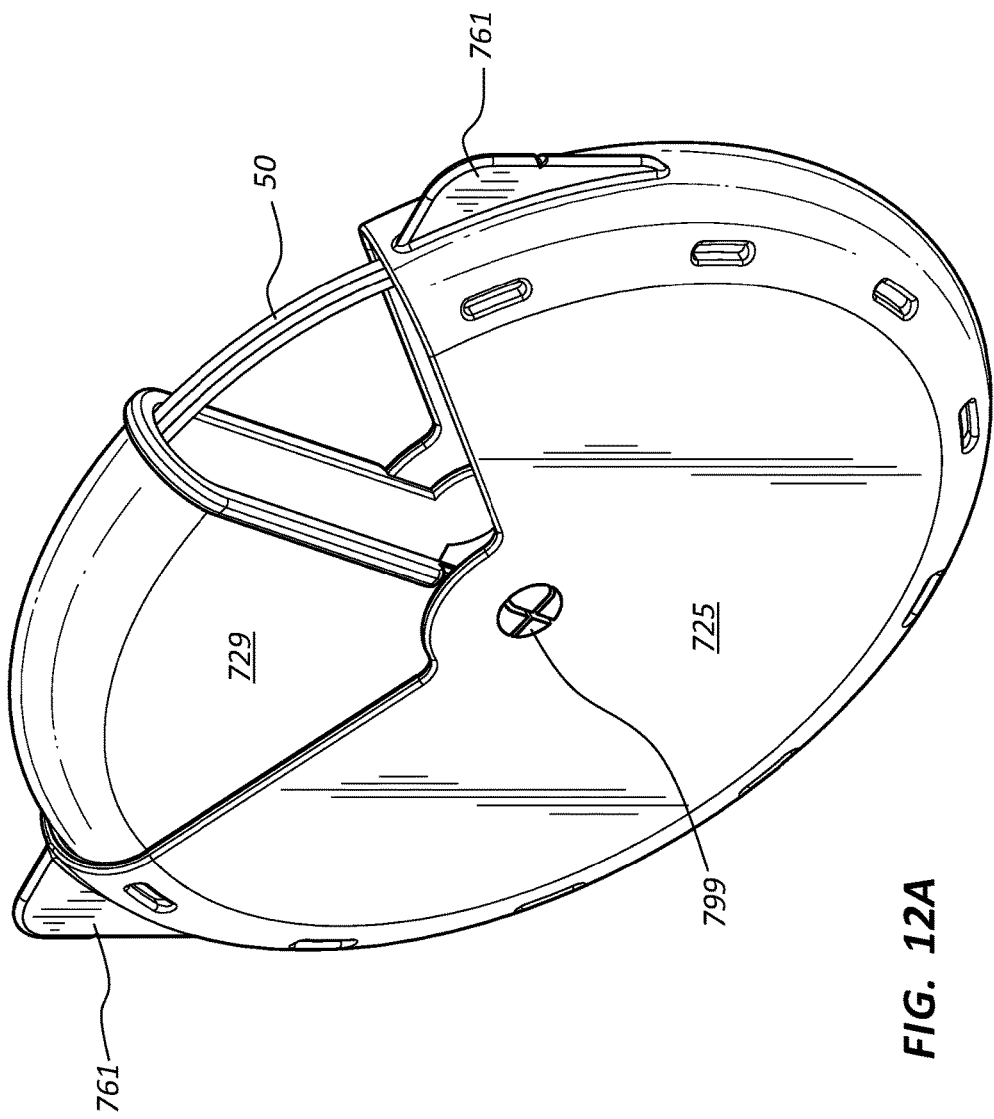
FIG. 12A is a perspective view of a separator according to another embodiment.
Figure 12C:
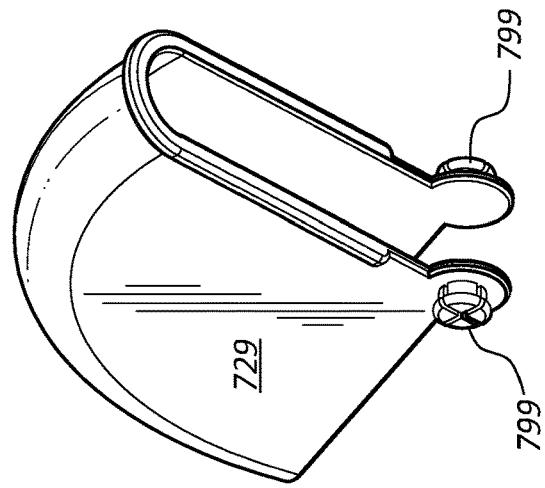
FIG. 12C is a perspective view of a another component of the separator of FIG. 12A.
Figure 12B:
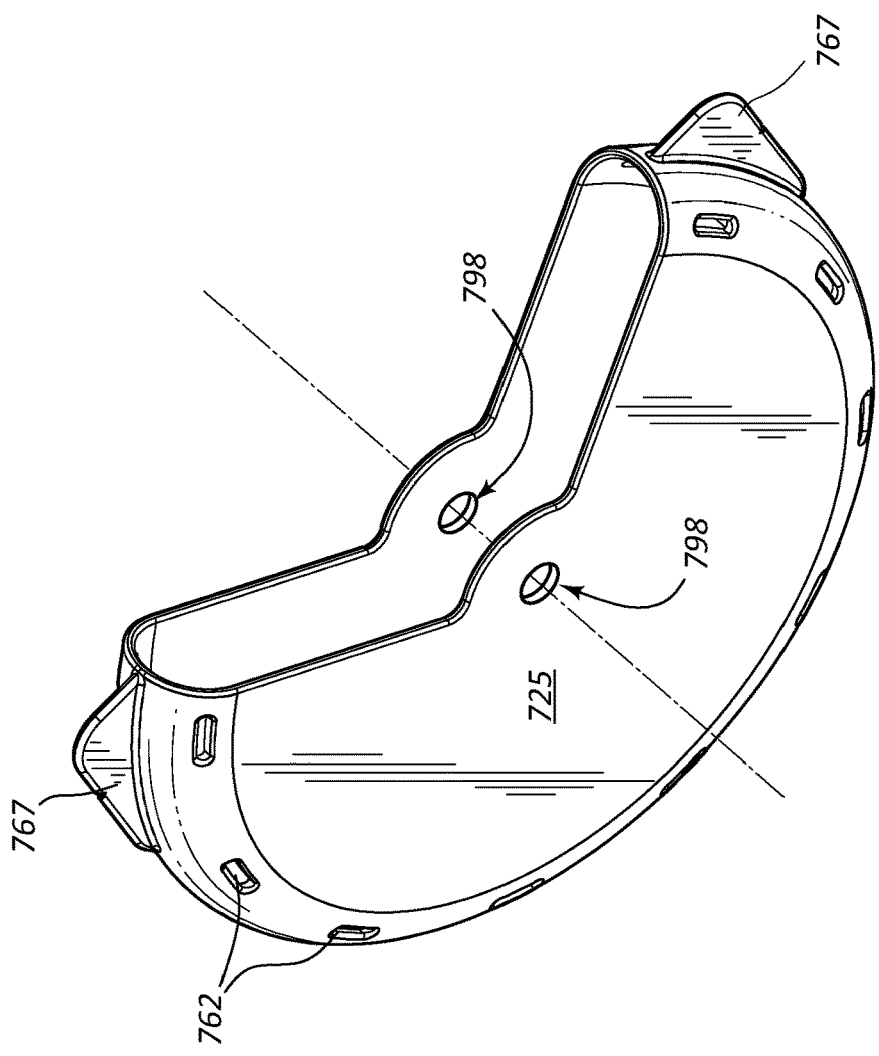
FIG. 12B is a perspective view of a component of the separator of FIG. 12A.

FIGS. 12A, 12B, and 12C depict another embodiment of a separator 720 that may be used in connection with a reservoir, such as the reservoir 610 depicted in FIGS. 11A-11D. More particularly, FIG. 12A provides an assembled perspective view of the separator 720, while FIGS. 12B and 12C provide perspective views of separate components of the separator 720. The separator 720 is substantially disc-shaped with a hollow interior. The separator 720 also includes a first wedge-shaped portion 729, and a second portion 725 that is shaped to form the remainder of the disc-shaped separator 720. The first portion 729 is configured to rotate relative to the section portion 725 about an axis that extends through a middle region of the separator 720. For example, in the depicted embodiment, the wedge-shaped portion 729 includes two pins 799 that extend outwardly from the first portion 729 through a set of holes 798 disposed at middle region of the separator 725. The first wedge-shaped portion 729 rotates about the pins 799 to transition from a configuration in which the guidewire 50 is substantially or completely enclosed within the separator 720 to a configuration that facilitates removal of the guidewire 50 from the separator 720. The separator 720 also includes a plurality of holes 762 disposed around the outer edges of the separator 720 that allow liquid to enter and escape from the interior of the separator 720.

Figure 13A:
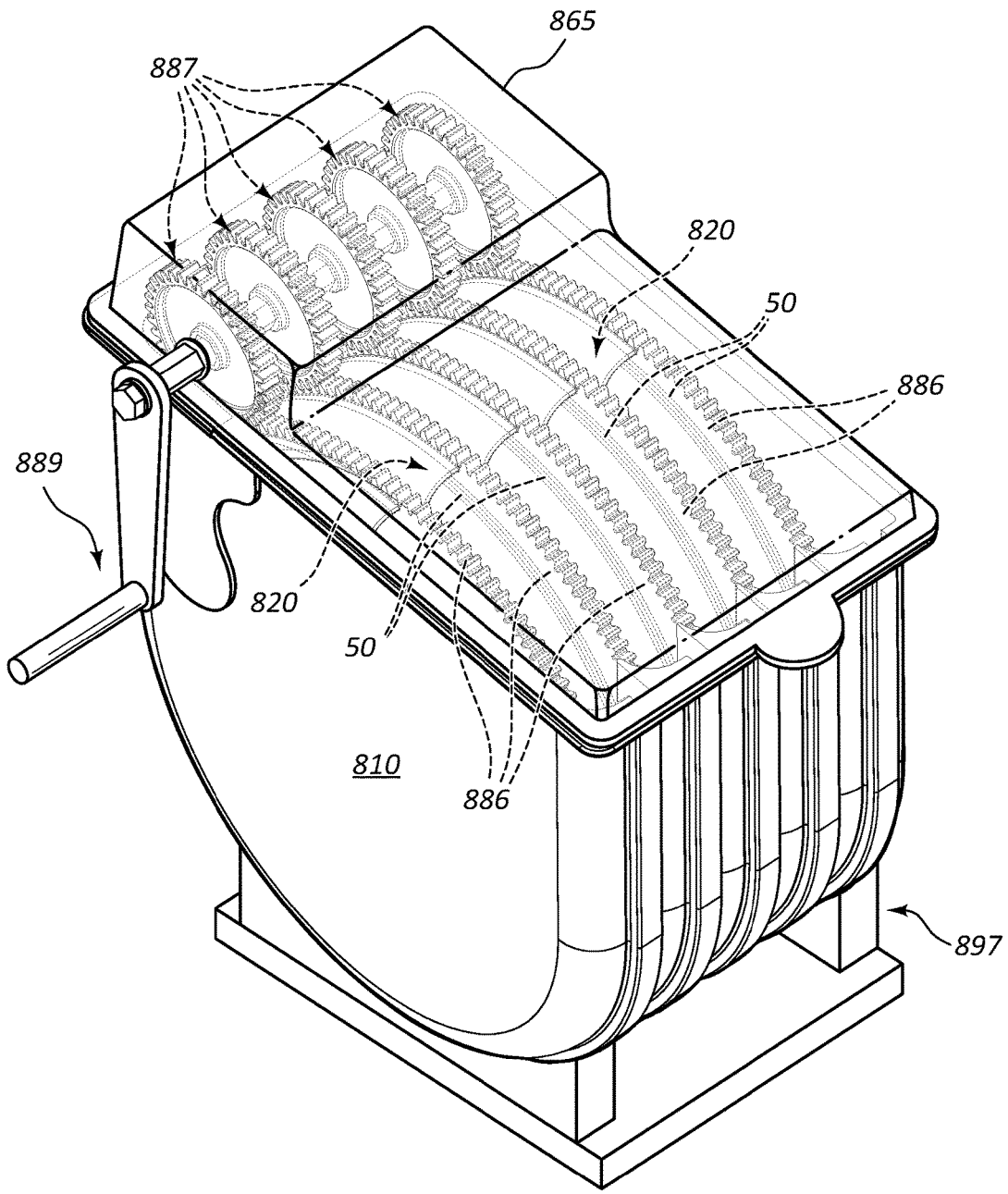
FIG. 13A is a perspective view of a guidewire holder according to another embodiment in a first configuration.
Figure 13B:
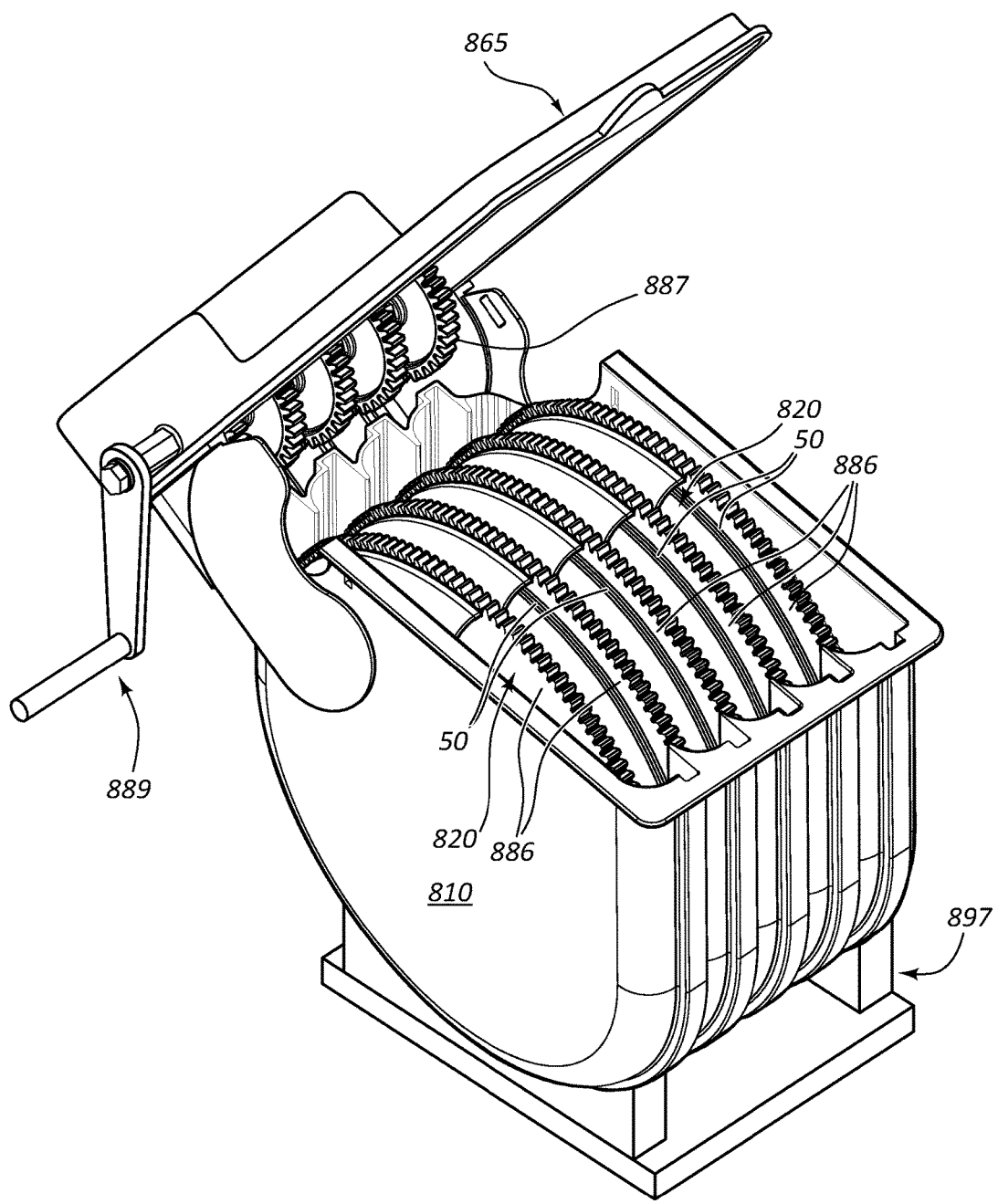
FIG. 13B is a perspective view of the guidewire holder of FIG. 13A in a second configuration.
Figure 13C:
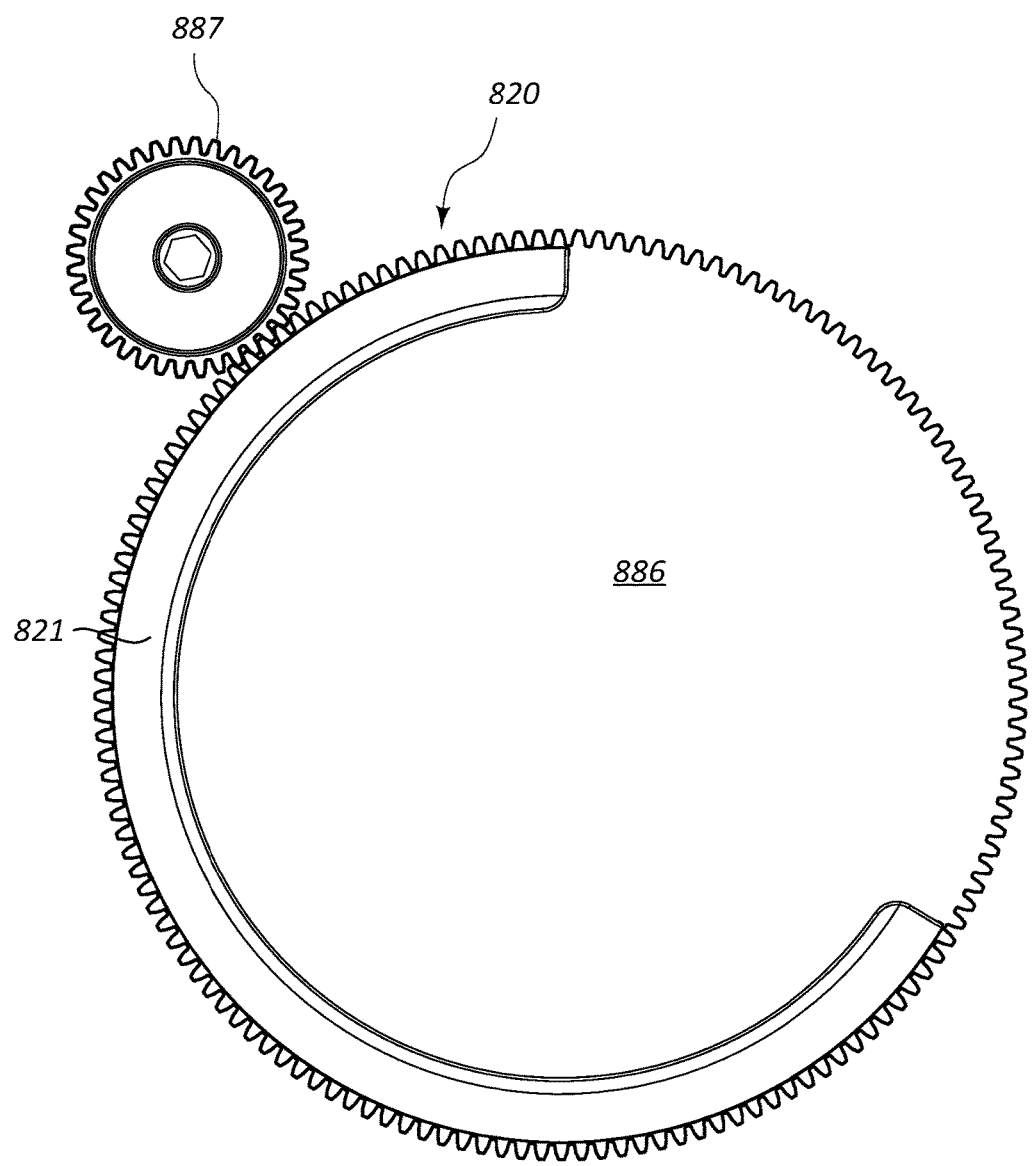
FIG. 13C is a front view of a subassembly of the guidewire holder of FIG. 13A, wherein the subassembly comprises a separator and a second gear.

FIGS. 13A-13C depict a guidewire holder 800 and components thereof. More particularly, FIG. 13A provides a perspective view of the guidewire holder 800 in a first configuration, while FIG. 13B provides a perspective view of the guidewire holder 800 in a second configuration. FIG. 13C provides a front view of a subassembly of a the guidewire holder of FIG. 13A, wherein the subassembly comprises a separator 820 and a second gear 887.

With reference to FIGS. 13A-13C, the guidewire holder 800 includes a reservoir 810, a lid 865, and a plurality of separators 820. When viewed from the front, the reservoir 810 is substantially U-shaped to accommodate the generally circular separators 820. The reservoir 810 comprises or is coupled to a leg portion 897 that is configured to maintain the guidewire holder 800 in an upright configuration.

Each separator 820 of the plurality of separators 820 comprises or is coupled to a first gear 886 and a lateral edge 821 which extends along a portion of the circumference of the separator 820. For example, in the depicted embodiment, the first gear 886 forms a surface that extends between the lateral edge 821 of the separator 820. The first gear 886 and the lateral edge 821 of the separator 820 cooperate to contact and retain a guidewire 50.

The first gear 886 is configured to engage with and couple to a second gear 887. The second gear 887 may be rotated in response to input or actuation by a practitioner. For example, in the depicted embodiment, the second gear 887 is coupled to a crank 889 that may be operated by the practitioner. In other or further embodiments, the second gear is coupled to an electric motor or some other mechanism that that facilitates rotation of the second gear.

When the lid 865 is in a lowered configuration (see FIG. 13A), the first gears 886 are engaged with and coupled to the second gears 887. When in this configuration, rotation of the second gear 887, such as by operation of the crank 889, causes the first gear 886 and the separator 820 to rotate within the reservoir 810.

When a guidewire 50 is (1) retained by the separator 820 and (2) partially submerged in a liquid 40 held by the reservoir 810 (e.g., because the reservoir is partially filled with liquid 40), the practitioner may rotate the second gear 887 (e.g., by operation of the crank 889), causing the guidewire 50 to rotate with the reservoir 810. By rotating the guidewire 50 in this manner, all exterior surfaces of the guidewire 50 may come in contact with the liquid 40.

Once all surfaces of the guidewire 50 have come in contact with the liquid 40, the lid 865 may be lifted by rotating the lid 865 relative to the reservoir 810. For example, the lid 865 may be rotatably coupled to the reservoir 810 such that lifting of the lid 865 disengages the second gear 887 from the first gear 886, allowing the practitioner to remove one of more separators 820 from the reservoir 810. In other words, in some embodiments, the lid 865 is coupled to one or more second gears 886 such that rotation of the lid 865 disengages the second gears 887 from the first gears 886. In some circumstances, the practitioner may remove the guidewire 50 directly from the guidewire holder 800 without removing a separator 820.

Figure 13D:
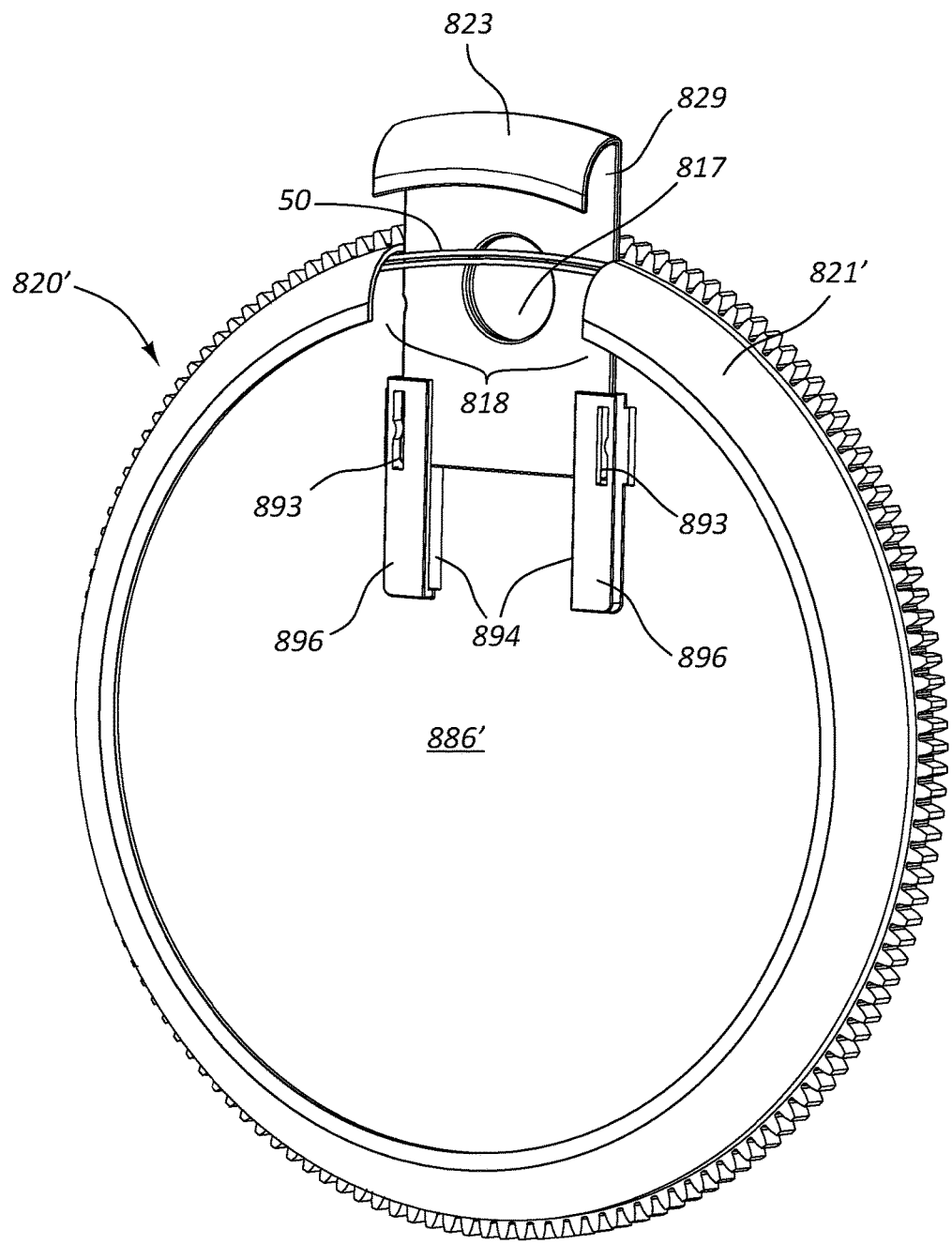
FIG. 13D is a perspective view of another embodiment of a separator in a first configuration.
Figure 13E:
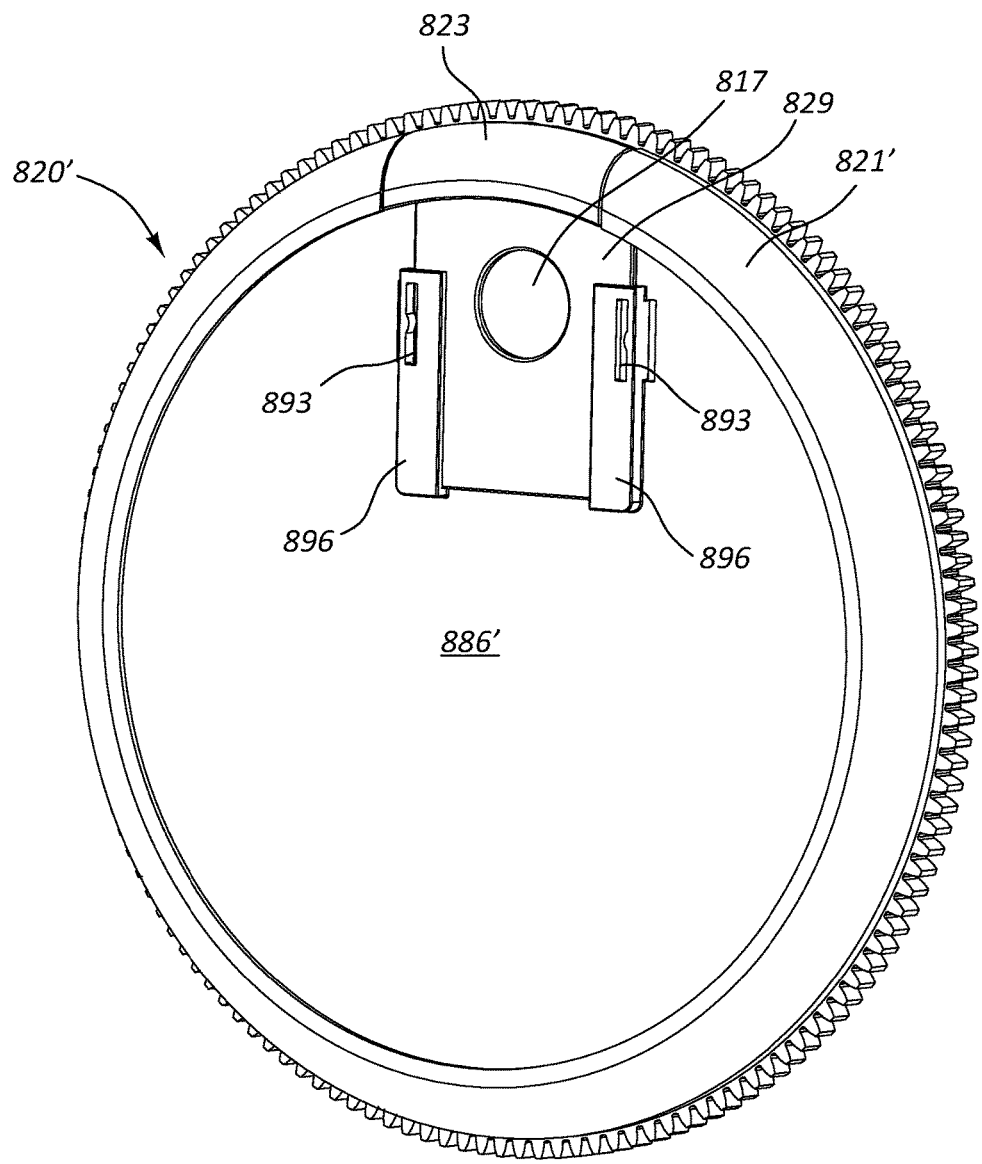
FIG. 13E is a perspective view of the separator of FIG. 13D in a second configuration.

FIGS. 13D and 13E depict another embodiment of a separator 820' that may be used in connection with a reservoir, such as the reservoir 810 depicted in FIGS. 13A and 13B. The separator 820' may have analogous features to the separator 820 depicted in FIG. 13C. For example, the embodiment depicted in FIGS. 13D and 13E includes a gear body 886' that may resemble the first gear 886 of the embodiment depicted in 13C. Additionally, the embodiment depicted in FIGS. 13D and 13E further includes a lateral edge 821' that may resemble the lateral edge 821 of the embodiment depicted in FIG. 13C. As compared to the lateral edge 821 of the embodiment of FIG. 13C, the lateral edge 821' depicted in FIGS. 13D and 13E may extend around a greater portion of the circumference of the associated gear body 886'

Referring to FIGS. 13D and 13E, the separator 820' may include a slide 829. The slide may be displacable between an open configuration and a closed configuration. The slide 829 may comprise a lip 823 which may have similar geometric characteristics of the lateral edge 821', for example, the curvature and/or width of the lip 823 may align with the lateral edge 821' when the slide is in a closed configuration. FIG. 13D shows the slide 829 in an open configuration, while FIG. 13E shows the slide 829 in a closed configuration.

The slide 829 may also include a handle 817 configured and/or placed to facilitate manipulation of the configuration of the slide 829, for example between an open and a closed configuration. In the illustrated embodiment, the handle 817 comprises an opening in the slide 829. In other embodiments the handle 817 may comprise ridges, protrusions, openings of different geometries, and/or other features. The slide 829 may couple to the gear body 886' of the separator 820' by engaging two slots 894 of the gear body 886'. These slots 894 may correspond to two brackets 896. In some embodiments, the brackets 896 may be integrally coupled to the gear body 886', while in other embodiments the brackets 896 may be coupled to the gear body 886' by other means. Still further, it is within the scope of this disclosure to couple the slide 829 to the gear body 886' through other features such as mating grooves, ridges, and so forth. The slide 829 may be displacable toward and away from the center of the gear body 886', allowing the slide 829 to be manipulated from an open configuration to a closed configuration. The brackets 896 may comprise locking mechanisms 893 which may enable the slide 829 to remain static in an open or closed configuration. Exemplary locking mechanisms include, but are not limited to, detents, tabs, ridges, and so forth.

In use, the practitioner may lock the slide 829 in the closed configuration by pushing on the lip 823 of the slide 829 toward the center of the first gear body 886' until the locking mechanisms 893 are engaged and the slide 829 is in the closed configuration. When the slide 829 is in the closed configuration, the locking mechanisms 893 of the slide 829 may allow the separator 820' to rotate inside of a reservoir, such as the reservoir 810 depicted in FIGS. 13A and 13B, while maintaining the slide 829 in the closed configuration. Similarly, the practitioner may lock the slide 829 in an open, or semi-open configuration, for example, by inserting a finger into the handle 817 and pulling the slide 829 outward relative to the gear body 886' until the locking mechanisms 893 are engaged and the slide 829 is in an open or semi-open position. The practitioner may desire the slide 829 to remain in an open position while removing the guidewire 50 from the separator 820'. The locking mechanisms 893 may also provide tactile or audible feedback to notify the practitioner that the slide 829 is fully disposed in the open or closed configuration.

Again, FIG. 13D illustrated a perspective view of one embodiment of a separator 820' in an open configuration. When the slide 829 is in the open configuration, a portion of the guidewire 50 may be exposed at an access area 818, allowing the practitioner to remove the guidewire 50 from the separator 820'. As explained above, the open configuration may be maintained during guidewire extraction though the use of a locking mechanism 893.

As noted above, FIG. 13E illustrates a perspective view of one embodiment of a separator 820' in a closed configuration. When the slide 829 is in the closed configuration, the lip 823 of the slide 829 may align with the geometry of the lateral edge 821' of the separator 820', and complete the lateral edge 821' about the circumference of the separator 820'. The closed configuration may provide additional protection to the guidewire 50 during storage, and may allow the separator 820' to rotate freely inside a reservoir, such as the reservoir 810 depicted in FIGS. 13A and 13B.

Furthermore, in some embodiments the guidewire holder 800 may comprise a spring and a release actuator. In such embodiments, rotation of the crank 889 may wind the spring, rather than directly rotating the second gears 887. The spring may store potential energy that, upon manipulation of the release actuator, is transferred as rotational kinetic energy to the second gears 887. In such embodiments, the guidewire holder 800 may initially be wound, allowing a practitioner to hydrate the guidewires through manipulation of the release actuator during therapy.

The guidewire holders disclosed herein may be used in connection with an absorbent cleaning device such as that described in U.S. application Ser. No. 14/450,788 titled "Absorbent Cleaning and Securement Devices and Methods" (filed on Aug. 4, 2014), which is hereby incorporated by reference in its entirety. In some instances, a guidewire holder may be used in connection with a stand-alone absorbent cleaning device. In other words, in some instances, a guidewire holder may be used with an absorbent cleaning device that is adjacent (but not coupled to) the guidewire holder. In other embodiments, such as that depicted in FIG. 14, the guidewire holder 900 may be coupled to or include an absorbent cleaning device 70.

Figure 14:
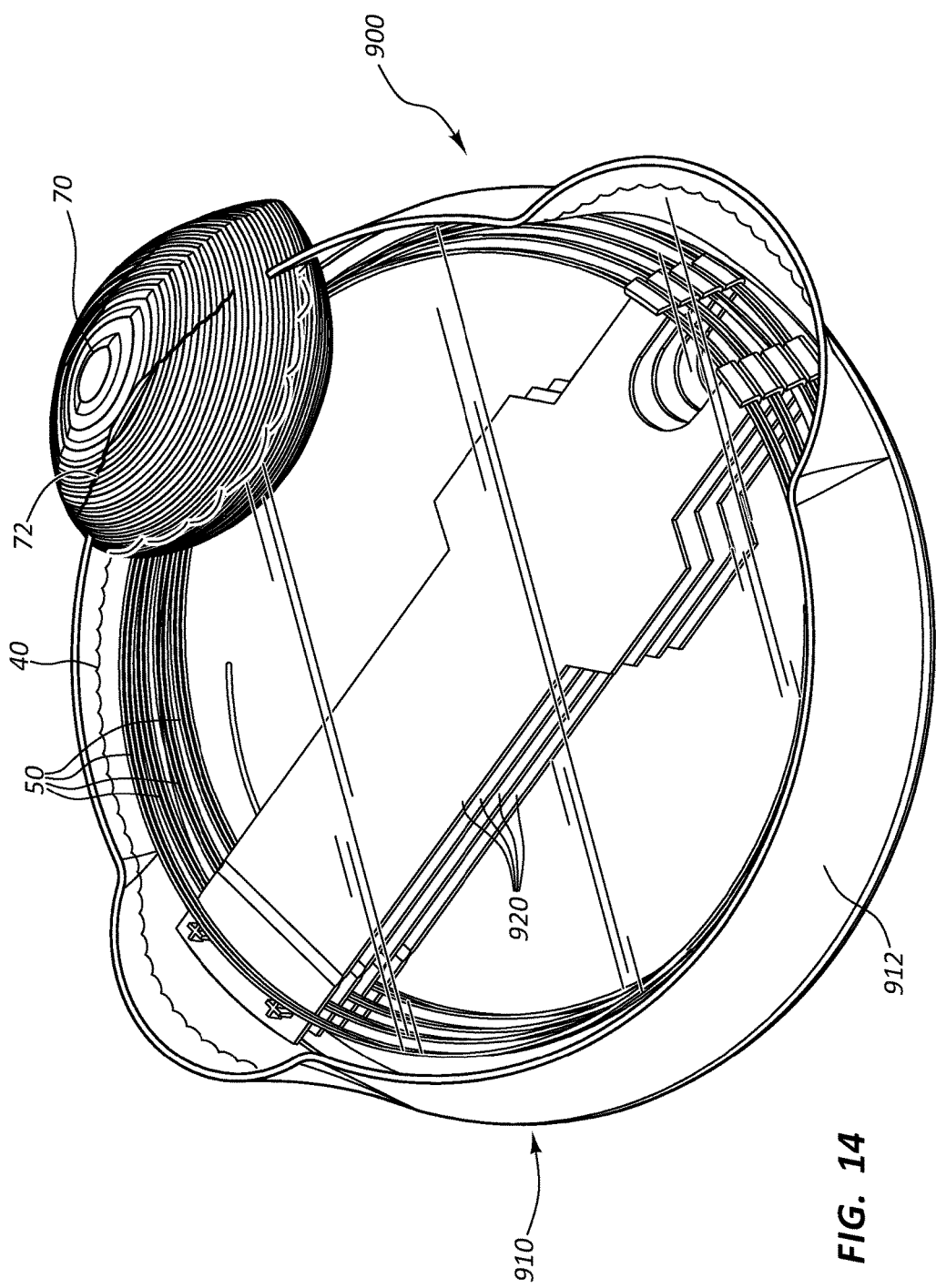
FIG. 14 is a perspective view of an absorbent cleaning device that is coupled to a guidewire holder.

In the embodiment depicted in FIG. 14, the guidewire holder 900 comprises a receptacle 910 and a plurality of separators 920. The separators 920 are configured to hold the guidewires 50 in place and thereby maintain the guidewires 50 in contact with a liquid 40. In the depicted embodiment, the absorbent cleaning device 70 is coupled to the receptacle 910. The absorbent cleaning device 70 is shaped to fit over an outer periphery 912 to attach to the receptacle 910. In other embodiments, an absorbent cleaning device may (1) be coupled to a guidewire holder in a different manner or (2) be disposed adjacent to (but not coupled to) the guidewire holder. Further, although the absorbent cleaning device 70 is shown in connection with a guidewire holder 900 that is similar to the guidewire holder 100 depicted in FIGS. 1-4, absorbent cleaning devices may be used in an analogous manner with other guidewire holders, such as any of the embodiments disclosed herein.

The absorbent cleaning device 70 may absorb liquid 40, such as a cleaning agent, saline solution, and/or an anticoagulant. In the depicted embodiment, the absorbent cleaning device 70 absorbs liquid 40 that that is held in the receptacle 910. However, in other embodiments, the absorbent cleaning device may absorb liquid from a source that is separate from the liquid that is held in the receptacle.

In some circumstances, the absorbent cleaning device 70 is used to clean a practitioner's gloves or a guidewire 50. For example, a practitioner may slide a guidewire 50 through the slit 72 to clean and/or apply a liquid to the surface of the guidewire.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification, are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or an element does not necessarily imply the existence of a second or additional such feature or element. It will be apparent to those having skill in the art that changes may be made to the details of the above-described embodiments without departing from the underlying principles of the present disclosure.

The invention claimed is:

1. A receptacle for storage and retrieval of a plurality of elongate medical instruments, the receptacle comprising:
   a reservoir for holding a liquid;
   a plurality of separators configured to be disposed within the reservoir, wherein each separator of the plurality of separators is configured to retain an elongate medical instrument and wherein at least one separator of the plurality of separators comprises a first gear;
   a lid coupled to the reservoir; and
   a second gear coupled to the lid, wherein lifting of the lid disengages the second gear from the first gear.

2. The receptacle of claim 1, wherein the plurality of elongate medical instruments comprises a plurality of guidewires.

3. The receptacle of claim 1, wherein
   the plurality of separators is configured to maintain the plurality of elongate medical instruments in contact with the liquid; and
   each separator of the plurality of separators is configured to separate a first coiled elongate medical instrument from a second coiled elongate medical instrument that is received and retained by an adjacent separator of the plurality of separators.

4. The receptacle of claim 1, wherein the plurality of separators comprises:
   a first elongate separator comprising a proximal portion and a distal portion;
   a second elongate separator configured to couple to and be disposed above the first elongate separator, the second elongate separator comprising:

a proximal portion that is configured for coupling to the proximal portion of the first separator; and a distal portion configured to be displaceable relative to the first elongate separator.

5. The receptacle of claim 4, wherein the proximal portions of the first and second separators each comprise one or more catches for holding a coiled elongate medical instrument in place.

6. The receptacle of claim 4, wherein a proximal end of the first elongate separator is offset from a proximal end of the second elongate separator such that the proximal end of the first elongate separator is disposed closer to a center of the reservoir than the proximal end of the second elongate separator.

7. The receptacle of claim 4, wherein the first elongate separator and the second elongate separator each comprise a distal recess to facilitate grasping of the elongate medical instrument.

8. The receptacle of claim 4, wherein the proximal portion of both the first elongate separator and the second elongate separator each comprise an upward protrusion and a downward protrusion to facilitate coupling to a component of the receptacle.

9. The receptacle of claim 1, wherein each separator of the plurality of separators either comprises or, when disposed within the reservoir, forms a cavity that is shaped for receiving and retaining an elongate medical instrument.

10. The receptacle of claim 9, further comprising an opening to the cavity, wherein
the opening is shaped to allow insertion of a coiled guidewire through the opening when the coiled guidewire is compressed; and
the cavity is shaped to allow expansion of the compressed coiled guidewire to secure the coiled guidewire within the cavity once the coiled guidewire is fully inserted into the cavity.

11. The receptacle of claim 9, wherein each separator of the plurality of separators is hingedly coupled to the reservoir.

12. The receptacle of claim 1, wherein the reservoir comprises an access area that is configured to suspend a portion of an elongate medical device away from an outer periphery of the reservoir to facilitate removal of the elongate medical device from the reservoir.

13. The receptacle of claim 1, wherein
a separator of the plurality of separators is substantially disc-shaped with a hollow interior;
the separator comprises a first portion and a second portion;
the first portion is substantially wedge-shaped; and
the first portion is configured to rotate relative to the second portion about an axis that extends through a middle region of the separator.

14. The receptacle of claim 1, wherein
rotation of the second gear, when the second gear is engaged with the first gear, causes the separator to rotate within the reservoir.

15. The receptacle of claim 14, further comprising an elongate medical instrument retained by the separator and partially submerged in a liquid held by the reservoir, wherein rotation of the second gear when the second gear is engaged with the first gear causes all exterior surfaces of the elongate medical instrument to contact the liquid.

16. The receptacle of claim 14, wherein the second gear is coupled to one or more of a crank or an electric motor.

17. A kit for facilitating the storage and retrieval of a coiled elongate medical instrument, the kit comprising:
a plurality of separators, wherein each separator of the plurality of separators is configured to be disposed within a reservoir to maintain the coiled elongate medical instrument in contact with liquid held by the reservoir; and
a first gear and a second gear that are configured to engage with one another, wherein each separator of the plurality of separators comprises or is coupled to the first gear;
wherein rotation of the second gear, when the second gear is engaged with the first gear, causes each separator of the plurality of separators to rotate within the reservoir; and
wherein lifting of a lid coupled to the reservoir disengages the second gear from the first gear.

18. The kit of claim 17, wherein the reservoir comprises an access area that is configured to suspend a portion of a coiled elongate medical instrument away from the outer periphery of a reservoir to facilitate extraction of the coiled elongate medical instrument from the reservoir.

19. The kit of claim 17, wherein each separator of the plurality of separators is configured to extend in a different direction from a pin such that the plurality of separators is disposed in a fanned-out configuration.

* * * * *